(12) United States Patent
Grewal et al.

(10) Patent No.: US 8,980,267 B2
(45) Date of Patent: Mar. 17, 2015

(54) ENGINEERED ANTIBODY-INTERFERON MUTANT FUSION MOLECULES

(71) Applicant: ImmunGene Inc., Thousand Oaks, CA (US)

(72) Inventors: Iqbal Grewal, Snohomish, WA (US); Sanjay Khare, Newbury Park, CA (US); Michael Gresser, Ojai, CA (US); Rashid Syed, Thousand Oaks, CA (US)

(73) Assignee: ImmunGene Inc, Camarillo, CA (US)

( * ) Notice: Subject to any disclaimer, the term of this patent is extended or adjusted under 35 U.S.C. 154(b) by 0 days.

(21) Appl. No.: 13/784,049

(22) Filed: Mar. 4, 2013

(65) Prior Publication Data

US 2013/0230517 A1    Sep. 5, 2013

Related U.S. Application Data

(60) Provisional application No. 61/634,565, filed on Mar. 3, 2012.

(51) Int. Cl.
| | |
|---|---|
| *A61K 39/00* | (2006.01) |
| *A61K 39/395* | (2006.01) |
| *A61K 38/21* | (2006.01) |
| *A61K 38/00* | (2006.01) |
| *C07K 14/56* | (2006.01) |
| *C07K 16/46* | (2006.01) |
| *C07K 16/30* | (2006.01) |
| *C07K 16/00* | (2006.01) |
| *C12P 21/08* | (2006.01) |
| *C07K 16/18* | (2006.01) |
| *C07K 16/28* | (2006.01) |
| *C07K 16/32* | (2006.01) |

(52) U.S. Cl.
CPC .............. *C07K 14/56* (2013.01); *C07K 16/30* (2013.01); *C07K 2319/00* (2013.01); *C07K 16/18* (2013.01); *C07K 16/2803* (2013.01); *C07K 16/2827* (2013.01); *C07K 16/2887* (2013.01); *C07K 16/2896* (2013.01); *C07K 16/32* (2013.01)
USPC ............... 424/134.1; 424/138.1; 424/85.7; 514/1.1; 530/351; 530/387.3; 530/387.7

(58) Field of Classification Search
None
See application file for complete search history.

(56) References Cited

U.S. PATENT DOCUMENTS

| | | | |
|---|---|---|---|
| 7,456,257 B2 | 11/2008 | Jones et al. | |
| 7,619,067 B2 | 11/2009 | Paidhungat et al. | |
| 7,767,799 B2 | 8/2010 | Schreiber et al. | |
| 8,258,263 B2 | 9/2012 | Morrison et al. | |
| 2010/0172868 A1* | 7/2010 | Morrison et al. | 424/85.4 |
| 2011/0070156 A1 | 3/2011 | Govindan et al. | |
| 2011/0274658 A1* | 11/2011 | Silver et al. | 424/85.7 |
| 2012/0009194 A1 | 1/2012 | Ferrone et al. | |
| 2014/0248238 A1 | 9/2014 | Wilson, Jr. et al. | |

FOREIGN PATENT DOCUMENTS

| | | | |
|---|---|---|---|
| WO | WO2009/039409 | * | 3/2009 |
| WO | 2011109400 A2 | | 9/2011 |
| WO | 2013059885 A2 | | 5/2013 |
| WO | 2013107791 A1 | | 7/2013 |
| WO | 2014089354 A1 | | 6/2014 |
| WO | 2014178820 A1 | | 11/2014 |

OTHER PUBLICATIONS

Mickle, J.E. et al. Genotype-phenotype relationships in cystic fibrosis. Medical Clinics of North America, 2000, vol. 84, No. 3, p. 597-607.*
Wells, J.A. Additivity of mutational effects in proteins. Biochemistry, 1990, vol. 29, No. 37, p. 8509-8517.*
Jaiten et al., Inquiring into the Differential Action of Interferons (IFNs): an IFN-a2 Mutant with Enhanced Affinity to IFNAR1 Is Functionally Similar to IFN-B, Molecular and Cellular Biology, 26(5): 1888-1897, 2006.
Kalie et al., An Interferon a2 Mutant Optimized by Phage Display for IFNAR1 Binding Confers Specifically Enhanced Antitumor Activities, The Journal of Biological Chemistry, 282(15): 11602-11611, 2007.
Nudelman et a., Inter-molecular interactions in a 44 kDa interferon-receptor complex detected by asymmetric reverse-protonation and 2D NOESY, Biochemistry, 49(25): 5117-5133, 2010.
Pan et al., Mutation of the IFNAR-1 Receptor Binding Site of Human IFN-a2 Generates Type I IFN Competitive Antagonists, Biochemistry, 47: 12018-12027, 2008.
PCT International Search Report and Written Opinion, PCT/US13/28899, dated Jul. 5, 2013.

(Continued)

*Primary Examiner* — Robert Landsman
*Assistant Examiner* — Bruce D Hissong
(74) *Attorney, Agent, or Firm* — Craig A Crandall, APC

(57) ABSTRACT

The field of the present invention relates to genetically engineered fusion molecules, methods of making said fusion molecules, and uses thereof in anti-tumor immunotherapies. More specifically, the present invention relates to fusion molecule constructs wherein a tumor associated antigen (TAA) antibody (Ab) serves as a targeting moiety to selectively deliver a cytokine to a tumor cell for purposes of killing or inhibiting the growth or proliferation of said tumor cell. In various embodiments, the engineered fusion molecules comprise a TAA Ab fused to an interferon-alpha (IFN-α) mutant molecule. The engineered Ab-IFN-α mutant fusion molecules of the present invention demonstrate improved therapeutic index and preserved or increased efficacy as compared to Ab-wildtype IFN-α fusion molecules, and/or demonstrate improved PK properties as compared to Ab-wildtype IFN-α fusion molecules.

24 Claims, 3 Drawing Sheets

(56) References Cited

OTHER PUBLICATIONS

Piehler et al., New Structural and Functional Aspects of the Type I Interferon Receptor Interaction Revealed by Comprehensive Mutational Analysis of the Binding Interface, Journal of Biological Chemistry, 275: 40425-40433, 2000.

Quadt-Akabayou et al., Determination of the human type I interferon receptor binding site on human interferon-a2 by cross saturation and an NMR-based model of the complex, Protein Science, 15: 2656-2668, 2006.

Schreiber et al., Mutational Analysis of the IFNAR1 Binding Site on IFNa2 Reveals the Architecture of a Weak Ligand-Receptor Binding-site, J. Mol. Biol., 353: 271-281, 2005.

Yeung et al., Engineering Human IgG1 Affinity to Human Neonatal Fc Receptor: Impact of Affinity Improvement on Pharmokinetics in Primates, J. Immunol., 182: 7663-7671, 2009.

* cited by examiner

SEQUENCE LISTING

```
<160> NUMBER OF SEQ ID NOS: 15

<210> SEQ ID NO 1
<211> LENGTH: 469
<212> TYPE: PRT
<213> ORGANISM: Artificial Sequence
<220> FEATURE:
<223> OTHER INFORMATION: anti-her2/neu antibody heavy chain - amino
      acid residues 1-19 represent a signal peptide

<400> SEQUENCE: 1

Met Glu Cys Ser Trp Val Met Leu Phe Leu Leu Ser Val Thr Ala Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
```

```
                65                  70                  75                  80
Asp Ser Val Lys Gly Arg Phe Thr Ile Ser Ala Asp Thr Ser Lys Asn
                    85                  90                  95

Thr Ala Tyr Leu Gln Met Asn Ser Leu Arg Ala Glu Asp Thr Ala Val
                100                 105                 110

Tyr Tyr Cys Ser Arg Trp Gly Asp Gly Phe Tyr Ala Met Asp Tyr
                115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Asp Glu Leu Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465

<210> SEQ ID NO 2
```

<211> LENGTH: 233
<212> TYPE: PRT
<213> ORGANISM: Artificial Sequence
<220> FEATURE:
<223> OTHER INFORMATION: anti-Her2/neu antibody light chain - amino
      acid residues 1-19 represent a signal peptide

<400> SEQUENCE: 2

```
Met Glu Trp Ser Cys Val Met Leu Phe Leu Ser Val Thr Ala Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Arg Ala Ser Gln Asp Val
            35                  40                  45

Asn Thr Ala Val Ala Trp Tyr Gln Gln Lys Pro Gly Lys Ala Pro Lys
50                  55                  60

Leu Leu Ile Tyr Ser Ala Ser Phe Leu Tyr Ser Gly Val Pro Ser Arg
65                  70                  75                  80

Phe Ser Gly Ser Arg Ser Gly Thr Asp Phe Thr Leu Thr Ile Ser Ser
                85                  90                  95

Leu Gln Pro Glu Asp Phe Ala Thr Tyr Tyr Cys Gln Gln His Tyr Thr
            100                 105                 110

Thr Pro Pro Thr Phe Gly Gln Gly Thr Lys Val Glu Ile Lys Arg Thr
        115                 120                 125

Val Ala Ala Pro Ser Val Phe Ile Phe Glu Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230
```

<210> SEQ ID NO 3
<211> LENGTH: 470
<212> TYPE: PRT
<213> ORGANISM: Artificial Sequence
<220> FEATURE:
<223> OTHER INFORMATION: anti-CD20 antibody heavy chain - amino acid
      residues 1-19 represent a signal peptide

<400> SEQUENCE: 3

```
Met Tyr Leu Gly Leu Asn Cys Val Ile Ile Val Phe Leu Leu Lys Gly
1               5                   10                  15

Val Gln Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
50                  55                  60

Glu Trp Ile Gly Ala Ile Tyr Pro Gly Asn Gly Asp Thr Ser Tyr Asn
65                  70                  75                  80
```

-continued

```
Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 4
<211> LENGTH: 232
```

```
<212> TYPE: PRT
<213> ORGANISM: Artificial Sequence
<220> FEATURE:
<223> OTHER INFORMATION: anti-CD20 antibody light chain - amino acid
      residues 1-19 represent a signal peptide

<400> SEQUENCE: 4

Met Lys Leu Pro Val Arg Leu Leu Val Leu Met Phe Trp Ile Pro Ala
1               5                   10                  15

Ser Ser Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 5
<211> LENGTH: 471
<212> TYPE: PRT
<213> ORGANISM: Artificial Sequence
<220> FEATURE:
<223> OTHER INFORMATION: anti-CD138 antibody heavy chain - amino acid
      residues 1-19 represent a signal peptide

<400> SEQUENCE: 5

Met Gly Trp Ser Tyr Ile Ile Leu Phe Leu Val Ala Thr Ala Thr Asp
1               5                   10                  15

Val His Ser Gln Val Gln Leu Gln Gln Ser Gly Ser Glu Leu Met Met
            20                  25                  30

Pro Gly Ala Ser Val Lys Ile Ser Cys Lys Ala Thr Gly Tyr Thr Phe
        35                  40                  45

Ser Asn Tyr Trp Ile Glu Trp Val Lys Gln Arg Pro Gly His Gly Leu
    50                  55                  60

Glu Trp Ile Gly Glu Ile Leu Pro Gly Thr Gly Arg Thr Ile Tyr Asn
65                  70                  75                  80
```

Glu Lys Phe Lys Gly Lys Ala Thr Phe Thr Ala Asp Ile Ser Ser Asn
                85                  90                  95

Thr Val Gln Met Gln Leu Ser Ser Leu Thr Ser Glu Asp Ser Ala Val
            100                 105                 110

Tyr Tyr Cys Ala Arg Arg Asp Tyr Tyr Gly Asn Phe Tyr Tyr Ala Met
            115                 120                 125

Asp Tyr Trp Gly Gln Gly Thr Ser Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Leu Gly Thr Gln Thr Tyr Ile Cys
            210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 6
<211> LENGTH: 236
<212> TYPE: PRT

<220> FEATURE:
<223> OTHER INFORMATION: anti-CD138 antibody light chain - amino acid
residues 1-22 represent a signal peptide

<400> SEQUENCE: 6

```
Met Asp Met Arg Val Pro Ala Gln Leu Leu Gly Leu Leu Leu Leu Trp
 1               5                  10                  15

Leu Arg Gly Ala Arg Cys Asp Ile Gln Met Thr Gln Ser Thr Ser Ser
            20                  25                  30

Leu Ser Ala Ser Leu Gly Asp Arg Val Thr Ile Ser Cys Ser Ala Ser
        35                  40                  45

Gln Gly Ile Asn Asn Tyr Leu Asn Trp Tyr Gln Lys Pro Asp Gly
    50                  55                  60

Thr Val Glu Leu Leu Ile Tyr Tyr Thr Ser Thr Leu Gln Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Pro Glu Asp Ile Gly Thr Tyr Tyr Cys Gln Gln
            100                 105                 110

Tyr Ser Lys Leu Pro Arg Thr Phe Gly Gly Gly Thr Lys Leu Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 7
<211> LENGTH: 463
<212> TYPE: PRT
<213> ORGANISM: Artificial Sequence
<220> FEATURE:
<223> OTHER INFORMATION: anti-endoplasmin antibody heavy chain - amino
acid residues 1-19 represent a signal peptide

<400> SEQUENCE: 7

```
Met Tyr Leu Gly Leu Asn Cys Val Ile Ile Val Phe Leu Leu Lys Gly
 1               5                  10                  15

Val Gln Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Ala Met His Trp Val Arg Gln Ala Pro Gly Gln Arg Leu
    50                  55                  60

Glu Trp Met Gly Trp Ile Asn Ala Gly Asn Gly Asn Thr Lys Tyr Ser
65                  70                  75                  80

Gln Lys Phe Gln Gly Arg Val Thr Ile Thr Arg Asp Thr Ser Ala Ser
```

```
                    85                  90                  95
Thr Ala Tyr Met Glu Leu Ser Ser Leu Arg Ser Glu Asp Thr Ala Val
                100                 105                 110
Tyr Tyr Cys Ala Arg Ala His Phe Asp Tyr Trp Gly Gln Gly Thr Leu
            115                 120                 125
Val Thr Val Ser Ala Ala Ser Thr Lys Gly Pro Ser Val Phe Pro Leu
130                 135                 140
Ala Pro Ser Ser Lys Ser Thr Ser Gly Gly Thr Ala Ala Leu Gly Cys
145                 150                 155                 160
Leu Val Lys Asp Tyr Phe Pro Glu Pro Val Thr Val Ser Trp Asn Ser
                165                 170                 175
Gly Ala Leu Thr Ser Gly Val His Thr Phe Pro Ala Val Leu Gln Ser
            180                 185                 190
Ser Gly Leu Tyr Ser Leu Ser Ser Val Val Thr Val Pro Ser Ser Ser
        195                 200                 205
Leu Gly Thr Gln Thr Tyr Ile Cys Asn Val Asn His Lys Pro Ser Asn
    210                 215                 220
Thr Lys Val Asp Lys Lys Val Glu Pro Lys Ser Cys Asp Lys Thr His
225                 230                 235                 240
Thr Cys Pro Pro Cys Pro Ala Pro Glu Leu Leu Gly Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
        275                 280                 285
Val Lys Phe Asn Trp Tyr Val Asp Gly Val Glu Val His Asn Ala Lys
    290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
            340                 345                 350
Ser Lys Ala Lys Gly Gln Pro Arg Glu Pro Gln Val Tyr Thr Leu Pro
        355                 360                 365
Pro Ser Arg Asp Glu Leu Thr Lys Asn Gln Val Ser Leu Thr Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys
    450                 455                 460

<210> SEQ ID NO 8
<211> LENGTH: 234
<212> TYPE: PRT
<213> ORGANISM: Artificial Sequence
<220> FEATURE:
<223> OTHER INFORMATION: anti-endoplasmin antibody light chain - amino
      acid residues 1-20 represent a signal peptide
```

<400> SEQUENCE: 8

```
Met Glu Ala Pro Ala Gln Leu Leu Phe Leu Leu Leu Trp Leu Pro
1               5                   10                  15

Asp Thr Thr Gly Glu Ile Glu Leu Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Ile Ser Ser Tyr Leu Asn Trp Tyr Gln Gln Lys Pro Gly Lys Ala Pro
    50                  55                  60

Lys Leu Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ser Tyr
            100                 105                 110

Ser Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 9
<211> LENGTH: 465
<212> TYPE: PRT
<213> ORGANISM: Artificial Sequence
<220> FEATURE:
<223> OTHER INFORMATION: anti-CD33 antibody heavy chain - amino acid
    residues 1-19 represent a signal peptide

<400> SEQUENCE: 9

```
Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Ile
        35                  40                  45

Thr Asp Ser Asn Ile His Trp Val Arg Gln Ala Pro Gly Gln Ser Leu
    50                  55                  60

Glu Trp Ile Gly Tyr Ile Tyr Pro Tyr Asn Gly Gly Thr Asp Tyr Asn
65                  70                  75                  80

Gln Lys Phe Lys Asn Arg Ala Thr Leu Thr Val Asp Asn Pro Thr Asn
                85                  90                  95

Thr Ala Tyr Met Glu Leu Ser Ser Leu Arg Ser Glu Asp Thr Ala Phe
            100                 105                 110
```

```
Tyr Tyr Cys Val Asn Gly Asn Pro Trp Leu Ala Tyr Trp Gly Gln Gly
            115                 120                 125

Thr Leu Val Thr Val Ser Ser Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 10
<211> LENGTH: 238
<212> TYPE: PRT
<213> ORGANISM: Artificial Sequence
<220> FEATURE:
<223> OTHER INFORMATION: anti-CD33 antibody light chain - amino acid
      residues 1-20 represent a signal peptide
```

-continued

```
<400> SEQUENCE: 10

Met Ser Val Pro Thr Gln Val Leu Gly Leu Leu Leu Trp Leu Thr
1               5                   10                  15

Asp Ala Arg Cys Asp Ile Gln Leu Thr Gln Ser Pro Ser Thr Leu Ser
            20                  25                  30

Ala Ser Val Gly Asp Arg Val Thr Ile Thr Cys Arg Ala Ser Glu Ser
        35                  40                  45

Leu Asp Asn Tyr Gly Ile Arg Phe Leu Thr Trp Phe Gln Gln Lys Pro
    50                  55                  60

Gly Lys Ala Pro Lys Leu Leu Met Tyr Ala Ala Ser Asn Gln Gly Ser
65                  70                  75                  80

Gly Val Pro Ser Arg Phe Ser Gly Ser Gly Ser Gly Thr Glu Phe Thr
                85                  90                  95

Leu Thr Ile Ser Ser Leu Gln Pro Asp Asp Phe Ala Thr Tyr Tyr Cys
            100                 105                 110

Gln Gln Thr Lys Glu Val Pro Trp Ser Phe Gly Gln Gly Thr Lys Val
        115                 120                 125

Glu Val Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 11
<211> LENGTH: 152
<212> TYPE: PRT
<213> ORGANISM: Artificial Sequence
<220> FEATURE:
<223> OTHER INFORMATION: anti-CD276 antibody heavy chain variable region
      - amino acid residues 1-19 represent a signal peptide

<400> SEQUENCE: 11

Met Asn Phe Gly Phe Arg Leu Ile Phe Leu Ala Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Glu Ala Ser Arg Phe Thr Phe
        35                  40                  45

Ser Ser Tyr Ala Met Ser Trp Val Arg Gln Thr Pro Glu Lys Arg Leu
    50                  55                  60

Glu Trp Val Ala Ala Ile Ser Gly Gly Gly Arg Tyr Thr Tyr Tyr Pro
65                  70                  75                  80

Asp Ser Met Lys Gly Arg Phe Thr Ile Ser Arg Asp Asn Ala Lys Asn
                85                  90                  95

Phe Leu Tyr Leu Gln Met Ser Ser Leu Arg Ser Glu Asp Thr Ala Met
            100                 105                 110
```

```
Tyr Tyr Cys Ala Arg His Tyr Asp Gly Tyr Leu Asp Tyr Trp Gly Gln
            115                 120                 125

Gly Thr Thr Leu Thr Val Ser Ser Ala Lys Thr Thr Ala Pro Ser Val
    130                 135                 140

Tyr Pro Leu Ala Pro Gly Ser Leu
145                 150

<210> SEQ ID NO 12
<211> LENGTH: 157
<212> TYPE: PRT
<213> ORGANISM: Artificial Sequence
<220> FEATURE:
<223> OTHER INFORMATION: anti-CD276 antibody light chain variable region
      - amino acid residues 1-20 represent a signal peptide

<400> SEQUENCE: 12

Met Lys Ser Gln Ser Gln Val Phe Val Phe Val Phe Leu Trp Leu Ser
1               5                   10                  15

Gly Val Asp Gly Asp Ile Val Met Thr Gln Phe Ala Gly Val Asp Gly
            20                  25                  30

Asp Ile Val Met Thr Gln Ser His Lys Phe Met Ser Thr Ser Val Gly
            35                  40                  45

Asp Arg Val Ser Ile Thr Cys Lys Ala Ser Gln Asp Val Ser Thr Thr
        50                  55                  60

Val Ala Trp Tyr Gln Gln Lys Pro Gly Gln Ser Pro Lys Leu Leu Ile
65                  70                  75                  80

Tyr Ser Ala Ser Tyr Arg Tyr Thr Gly Val Pro Asp Arg Phe Thr Gly
                85                  90                  95

Ser Gly Ser Gly Thr Asp Phe Thr Phe Thr Ile Ser Ser Val Gln Ala
            100                 105                 110

Glu Asp Leu Ala Val Tyr Tyr Cys Gln Gln His Tyr Ser Thr Pro Pro
            115                 120                 125

Thr Phe Gly Gly Gly Thr Lys Leu Glu Ile Lys Arg Ala Asp Ala Ala
        130                 135                 140

Pro Thr Val Ser Ile Phe Pro Pro Ser Ser Lys Leu Gly
145                 150                 155

<210> SEQ ID NO 13
<211> LENGTH: 165
<212> TYPE: PRT
<213> ORGANISM: Artificial Sequence
<220> FEATURE:
<223> OTHER INFORMATION: human interferon alpha 2 wildtype protein

<400> SEQUENCE: 13

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
```

```
                    100                 105                 110
Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 14
<211> LENGTH: 6
<212> TYPE: PRT
<213> ORGANISM: Artificial Sequence
<220> FEATURE:
<223> OTHER INFORMATION: peptide linker

<400> SEQUENCE: 14

Ser Gly Gly Gly Gly Ser
1               5

<210> SEQ ID NO 15
<211> LENGTH: 14
<212> TYPE: PRT
<213> ORGANISM: Artificial Sequence
<220> FEATURE:
<223> OTHER INFORMATION: peptide linker

<400> SEQUENCE: 15

Ala Glu Ala Ala Ala Lys Glu Ala Ala Ala Lys Ala Gly Ser
1               5                   10
```

ENGINEERED ANTIBODY-INTERFERON MUTANT FUSION MOLECULES

CROSS-REFERENCE TO RELATED APPLICATIONS

The application claims priority to and benefit of U.S. Provisional Application No. 61/634,565, filed Mar. 3, 2012, which is incorporated herein by reference in its entirety for all purposes.

STATEMENT OF GOVERNMENT SUPPORT

This invention was made with United States government support pursuant to Grant No. 1R43CA162762-01A1 awarded by the National Institutes of Health. The United States government has certain rights in this invention.

TECHNICAL FIELD

The field of the present invention relates to genetically engineered fusion molecules, methods of making said fusion molecules, and uses thereof in anti-tumor immunotherapies.

BACKGROUND OF THE INVENTION

Interferon is an important cytokine which has multiple effects on the immune response (Theofilopoulos et al., Annu. Rev. Immunol., 23:307-336, 2005). Interferons include type 1 interferons (e.g., interferon-alpha (IFN-α) and interferon-beta (IFN-β)) and type 2 interferons (e.g., interferon-gamma (IFN-γ)). All type 1 IFNs are recognized by a shared receptor (IFN-αR) composed of two transmembrane proteins, IFN-αR1 and IFN-αR2. IFN-α's are known to inhibit angiogenesis (Sidky Y A and E C Borden, Cancer Res., 47:5155, 1987), mediate stimulation and differentiation of dendritic cells (Santini et al., J Exp Med, 191:1777, 2000), and are important in in vivo proliferation, expansion and long-term survival of antigen specific CD8+ T cells (Tough D F et al., Science, 272:1947, 1996). Although first described for their ability to inhibit viral replication, IFN-α's have multiple properties exhibiting anti-proliferative effects, induction of apoptosis (Rodriguez-Villanueva J and T J McDonnell, Int J Cancer, 61:110, 1995) and induction of the tumor suppressor gene, P53, in tumor cells (Takaoka A et al., Nature, 424:516, 2003). Thus, IFN-α's were the first recombinant proteins used for the treatment of various cancers.

Unfortunately, the use of IFN-α' to treat cancer has been limited by its short half-life and associated systemic toxicities (Weiss K, Semin Oncol, 25:9, 1998; Jones G J and Itri L M, Cancer, 57:1709, 2006). Because of the short in vivo half-life of IFN-α, frequent administration is required. Pharmacokinetic (PK) studies have indicated that only 0.01% of subcutaneously injected IFN-α reaches the target tumor site (Suzuki K et al., Gene Ther., 10(9):765-773, 2003). The most common adverse events associated with IFN-α therapy are flu-like symptoms, fatigue, anorexia, and central nervous system and psychiatric reactions, and some of these side-effects may become dose-limiting (Jones G J and Itri L M, Cancer, 57:1709, 2006). Given these limitations, it is difficult to achieve effective IFN-α concentrations at sites of malignant disease without causing systemic toxicity. The limitations of systemic IFN-α therapy have led to the exploration of alternative strategies to deliver IFN-α safely and effectively into the tumor vicinity.

SUMMARY OF THE INVENTION

In one aspect, the present invention provides novel genetically engineered tumor associated antigen (TAA) antibody (Ab)-interferon alpha (IFN-α) mutant molecules.

In one aspect, the present invention provides genetically engineered fusion molecules comprising a TAA Ab attached to a IFN-α mutant molecule, wherein said antibody is attached directly to said IFN-α mutant molecule, wherein said fusion molecule demonstrate improved PK properties as compared to a TAA Ab-wildtype (wt) IFN-α fusion molecule.

In one aspect, the present invention provides genetically engineered fusion molecules comprising a TAA Ab attached to a IFN-α mutant molecule, wherein said antibody is attached directly to said IFN-α mutant molecule, wherein said fusion molecule when contacted to a tumor cell results in the killing or inhibition of growth or proliferation of said tumor cell.

In various embodiments of the present invention, the interferon alpha mutant molecule of the genetically engineered fusion molecules comprises a mutated human IFN-α2 molecule comprising at least one mutation in SEQ ID NO: 13, wherein said mutation is selected from the group consisting of H57Y, E58N, Q61S, H57S, E58S, H57A, E58A, Q61A, R149A, R162A, L30A, D35E, E165D, L26A, F27A, L135A, A145V; and combinations thereof.

In various embodiments, the fusion molecule comprises a TAA antibody selected from the group consisting of anti-HER2/neu, anti-HER3, anti-HER4, anti-CD4, anti-CD19, anti-CD20, anti-CD22, anti-CD25, anti-CD33, anti-CD138, anti-CD200, anti-CD276, anti-CXCR3, anti-CXCR5, anti-CCR3, anti-CCR4, anti-CCR9, anti-CRTH2, anti-PMCH, and anti-endoplasmin antibody.

In one embodiment, the fusion molecule comprises an anti-HER2/neu antibody and a mutated human IFN-α2 molecule comprising the mutation F27A in SEQ ID NO: 13.

In one embodiment, the fusion molecule comprises an anti-CD20 antibody and a mutated human IFN-α2 molecule comprising the mutation F27A in SEQ ID NO: 13.

In one embodiment, the fusion molecule comprises an anti-CD138 antibody and a mutated human IFN-α2 molecule comprising the mutation F27A in SEQ ID NO: 13.

In one embodiment, the fusion molecule comprises an anti-endoplasmin antibody and a mutated human IFN-α2 molecule comprising the mutation F27A in SEQ ID NO: 13.

In one embodiment, the fusion molecule comprises an anti-CD33 antibody and a mutated human IFN-α2 molecule comprising the mutation F27A in SEQ ID NO: 13.

In one embodiment, the fusion molecule comprises an anti-CD276 antibody and a mutated human IFN-α2 molecule comprising the mutation F27A in SEQ ID NO: 13.

In one embodiment, the fusion molecule comprises an anti-HER2/neu antibody and a mutated human IFN-α2 molecule comprising the two mutations R149A and R162A in SEQ ID NO: 13.

In one embodiment, the fusion molecule comprises an anti-CD20 antibody and a mutated human IFN-α2 molecule comprising the two mutations R149A and R162A in SEQ ID NO: 13.

In one embodiment, the fusion molecule comprises an anti-CD138 antibody and a mutated human IFN-α2 molecule comprising the two mutations R149A and R162A in SEQ ID NO: 13.

In one embodiment, the fusion molecule comprises an anti-endoplasmin antibody and a mutated human IFN-α2 molecule comprising the two mutations R149A and R162A in SEQ ID NO: 13.

In one embodiment, the fusion molecule comprises an anti-CD33 antibody and a mutated human IFN-α2 molecule comprising the two mutations R149A and R162A in SEQ ID NO: 13.

In one embodiment, the fusion molecule comprises an anti-CD276 antibody and a mutated human IFN-α2 molecule comprising the two mutations R149A and R162A in SEQ ID NO: 13.

In another embodiment, the fusion molecule comprises an antibody selected from the group consisting of a fully human antibody, a humanized antibody, a chimeric antibody, a monoclonal antibody, a polyclonal antibody, a recombinant antibody, an antigen-binding antibody fragment, Fab, Fab', Fab$_2$, Fab'$_2$, IgG, IgM, IgA, IgE, scFv, dsFv, dAb, nanobodies, unibodies, and diabodies.

Another aspect of the present invention relates to a pharmaceutical composition, and method of preparing said pharmaceutical composition, wherein said composition comprises the genetically engineered fusion molecule of the present invention as an active ingredient, in a pharmaceutically acceptable carrier.

Another aspect of the present invention relates to a method of treating tumors or tumor metastases in a patient, comprising administering to said patient a therapeutically effective amount (either as monotherapy or as part of a combination therapy regimen) of a genetically engineered fusion molecule of the present invention in pharmaceutically acceptable carrier, wherein such administration promotes tumor regression and/or tumor death.

Another aspect of the present invention relates to the use of a genetically engineered fusion of the present invention for the preparation of a medicament for treating tumors or tumor metastases in a patient in need thereof.

Other aspects of the present invention relate to nucleic acids that encode the genetically engineered fusion molecules of the present invention; vectors comprising nucleic acid molecules encoding fusion molecules of the invention, optionally, operably-linked to control sequences recognized by a host cell transformed with the vector; host cells comprising vectors comprising nucleic acid molecules encoding fusion molecules of the invention; a process for producing a fusion molecule of the invention comprising culturing host cells comprising vectors comprising nucleic acid molecules encoding fusion molecules of the invention so that the nucleic acid is expressed and, optionally, recovering the fusion molecule from the host cell culture medium. In various embodiments the nucleic acid encodes a fusion molecule comprising a tumor associated antigen antibody attached to an interferon mutant molecule. In various embodiments the nucleic acid encodes a peptide linker (e.g., as described herein) attaching the antibody to the interferon mutant molecule.

BRIEF DESCRIPTION OF THE DRAWINGS

In FIG. 1, the ovals labeled as $V_L$, $V_H$, $C_L$, $C_{H1}$, $C_{H2}$ and $C_{H3}$ represent a full length antibody (Ab) as defined herein. The oval labeled C represents a cytokine, e.g., an IFN-α mutant. A linker is represented by the squiggled line. As depicted in FIG. 1, C is attached to the Ab via a linker at the two $C_{H3}$ sites. In one alternative embodiment, C is attached to the Ab via a linker at the two $V_L$ sites. In yet another alternative embodiment, C will be attached to the Ab via a linker at the two $V_H$ sites. In yet another alternative, C will be attached to the Ab via a linker at an internal site rather than at the $C_{H3}$, $V_L$, or $V_H$ sites.

FIG. 3 depicts another proposed design for a genetically engineered fusion molecule of the present invention. In FIG. 4, the ovals labeled as $V_L$, $V_H$, $C_L$, and $C_{H1}$ represent a Fab as defined herein. The oval label C represents a cytokine. A linker is represented by the squiggled line. As depicted in FIG. 3, C is attached to the Fab via a linker at the $C_{H1}$ site. In one alternative embodiment, C will be attached to the Fab via a linker at the $V_L$ site rather than the $C_{H1}$. In yet another alternative, C will be attached to the Fab via a linker at the $V_H$ site rather than the $V_L$ or $C_{H1}$ sites. In yet another alternative, C will be attached to the Fab via a linker at an internal site rather than at the $C_{H1}$, $V_L$, or $V_H$ sites.

SEQUENCE LISTINGS

Figure 1:
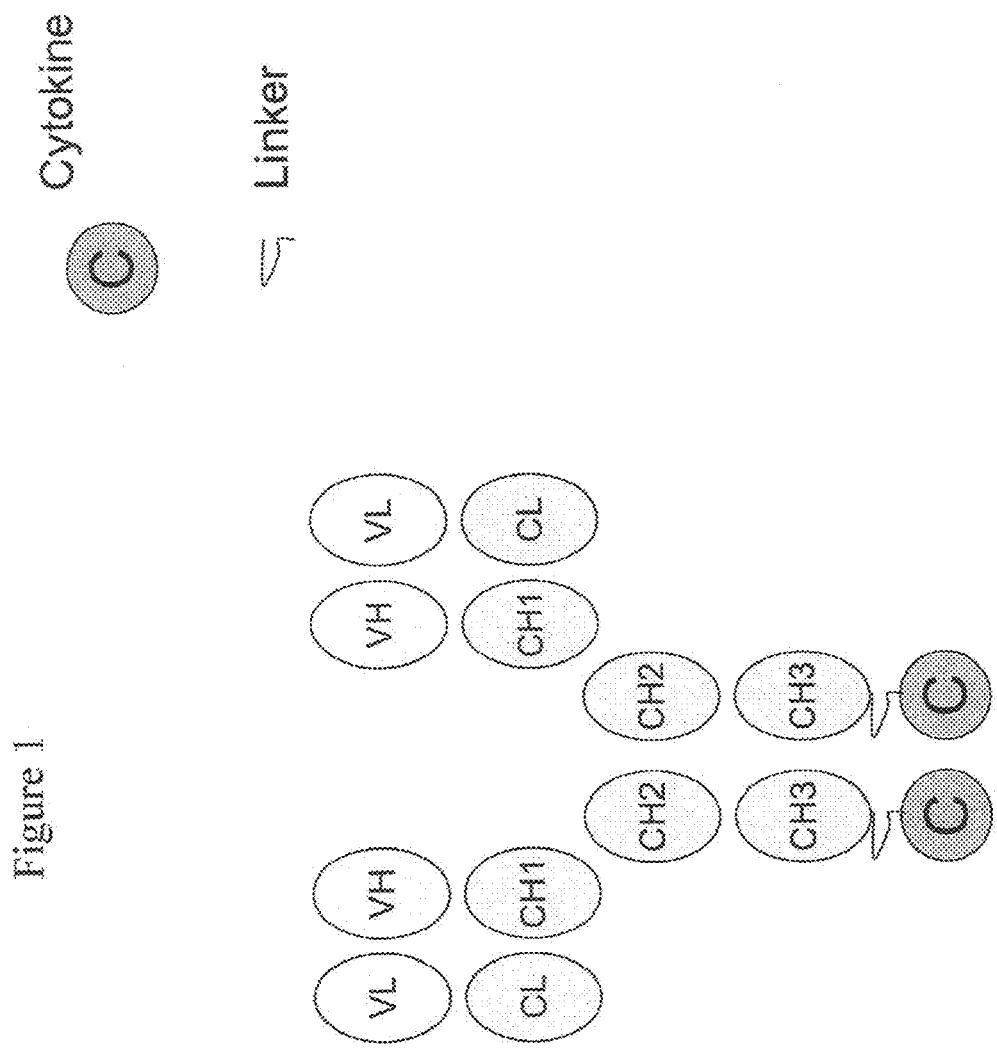
FIG. 1 depicts one proposed design for a genetically engineered fusion molecule of the present invention.

The amino acid sequences listed in the accompanying sequence listing are shown using standard three letter code for amino acids, as defined in 37 C.F.R. 1.822.

SEQ ID NO: 1 is the amino acid sequence of the heavy chain of an anti-Her2/neu antibody wherein amino acid residues 1-19 represent a signal peptide. SEQ ID NO: 2 is the amino acid sequence encoding the light chain of an anti-Her2/neu antibody wherein amino acid residues 1-19 represent a signal peptide.

SEQ ID NO: 3 is the amino acid sequence of the heavy chain of an anti-CD20 antibody wherein amino acid residues 1-19 represent a signal peptide. SEQ ID NO: 3 is the amino acid sequence encoding the light chain of an anti-CD20 antibody wherein amino acid residues 1-19 represent a signal peptide.

SEQ ID NO: 5 is the amino acid sequence of the heavy chain of an ant-CD138 antibody wherein amino acid residues 1-19 represent a signal peptide. SEQ ID NO: 6 is the amino acid sequence encoding the light chain of an anti-CD138 antibody wherein amino acid residues 1-22 represent a signal peptide.

SEQ ID NO: 7 is the amino acid sequence of the heavy chain of an anti-endoplasmin antibody wherein amino acid residues 1-19 represent a signal peptide. SEQ ID NO: 8 is the amino acid sequence encoding the light chain of an anti-endoplasmin antibody wherein amino acid residues 1-20 represent a signal peptide.

SEQ ID NO: 9 is the amino acid sequence of the heavy chain of an anti-CD33 antibody wherein amino acid residues 1-19 represent a signal peptide. SEQ ID NO: 10 is the amino acid sequence encoding the light chain of an anti-CD33 antibody wherein amino acid residues 1-20 represent a signal peptide.

SEQ ID NO: 11 is the amino acid sequence of the heavy chain variable region of an anti-CD276 antibody wherein amino acid residues 1-19 represent a signal peptide. SEQ ID NO: 12 is the amino acid sequence encoding the light chain variable region of an anti-CD276 antibody wherein amino acid residues 1-20 represent a signal peptide.

SEQ ID NO: 13 is the amino acid sequence of a human wildtype IFN-α2 molecule.

SEQ ID NO: 14 is the amino acid sequence of a peptide linker.

SEQ ID NO: 15 is the amino acid sequence of a peptide linker.

DETAILED DESCRIPTION OF THE INVENTION

U.S. Pat. No. 8,258,263 (Morrison et al.) demonstrates that targeted wildtype (wt)IFN-α may have a considerably greater therapeutic index than non-targeted wtIFN-α, making it possible to administer it at effective doses. Specifically, Morrison et al. demonstrated that various tumor associated antigen Ab-wtIFN-α chimeric constructs demonstrated substantially improved therapeutic efficacy (~100-fold more potent), with an apparent reduction of systemic toxicity, as compared to non-fused wtIFN-α.

In various embodiments of the present invention, genetically engineered fusion molecules comprising a tumor associated antigen antibody attached via a linker to an IFN-α mutant molecule are prepared for purposes of utilizing the specificity of the antibody to target the IFN-α mutant molecule to the tumor cells.

The IFN-α mutant molecules used in the preparation of the fusion molecules of the present invention have varying affinity for IFNαR complex. The present inventors evaluate the relationship between IFNαR affinity and in vitro therapeutic index, and the anti-tumor efficacy of the fusion protein in vivo, and identify Ab-IFN-α mutant fusion molecules which demonstrate improved therapeutic index, and preserved or improved in vivo efficacy, as compared to Ab-wtIFN-α fusion molecules. The present inventors also identify Ab-IFN-α mutant fusion molecules which demonstrate improved PK properties as compared to an Ab-wtIFN-α fusion molecule. The therapeutic index is defined as: the $EC_{50}$ of the Ab-IFNα mutant fusion molecule for cells which express the antigen recognized by the Ab and which express IFNαR ("targeted") divided by the $EC_{50}$ of the Ab-IFNα mutant fusion molecule for cells which express only IFNαR ("non-targeted"). Efficacy is defined as potency of the fusion molecule at killing cancer cells which express the antigen to which the Ab portion of the fusion molecule binds.

The approach used to identify such Ab-IFN-α mutant fusion molecules is as follows: 1) an IFN-α mutant was prepared; 2) an antibody which binds to a tumor associated antigen was prepared; 3) several Ab-IFN-α mutant fusion molecules comprising the IFN-α mutants and antibodies from steps 1) and 2) were constructed via chemical conjugation or direct attachment via a linker; 4) the resulting chemical conjugates or fusion molecules were systematically tested, at varying doses, in several in vitro functional assays to identify those having improved therapeutic index; and 5) in vivo studies using the chemical conjugates or fusion molecules demonstrating the best therapeutic index were performed to determine efficacy in treating in vivo tumors. As relates specifically to step 4), in vitro functional assays were used to determine: a) the ability of the fusion molecules to bind the IFN-αR complex on non-targeted cells; b) the ability of the fusion molecule to bind cells expressing the IFN-αR complex and the antigen targeted by the Ab; c) the ability of the fusion molecule to bind FcRn receptor; d) the IFN-α bioactivity of the fusion molecules on non-targeted cells; e) the antiproliferative activity of the fusion molecules on targeted cells; and f) the ability of the fusion molecule to induce apoptosis. As relates specifically to step 5), in vivo assays were used to: a) confirm efficacy of a given fusion for treating tumors; and b) confirm improved PK properties for a given fusion molecule.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are well known and commonly used in the art. Standard techniques can be used for chemical syntheses, chemical analyses, pharmaceutical preparation, composition, and delivery, and treatment of patients.

The terms "polypeptide", "peptide" and "protein" are used interchangeably herein to refer to a polymer of amino acid residues. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1000, 750, 500, 250, 200, 175, 150, 125, 100, 90, 80, 70, 60, 50, 40, 30, 20, 15, 14, 13, 12, 11, or amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. (1991) Nature 354: 105).

A "variant" of a polypeptide comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, an "antibody" refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $C_{H2}$ and $C_{H3}$ (and in some instances, $C_{H4}$). Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework region and CDRs has been defined (see, Kabat et al., *Sequences of Proteins of Immunological Interest*, U.S. Department of Health and Human Services, 1991, which is hereby incorporated by reference). The Kabat database is now maintained online and CDR sequences can be determined, for example, see IMGT/V-QUEST programme version: 3.2.18., Mar. 29, 2011, available on the internet and Brochet, X. et al., Nucl. Acids Res., 36:503-508, 2008). The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The CDRs are primarily responsible for binding to an epitope of an antigen. The CDRs of each chain are typically referred to as $CDR_1$, $CDR_2$, $CDR_3$, numbered sequentially starting from the N-terminus, and are also typically identified by the chain in which the particular CDR is located. Thus, a $V_H$ $CDR_3$ is located in the variable domain of the heavy chain of the antibody in which it is found, whereas a $V_L$ $CDR_1$ is the $CDR_1$ from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a $C_{H2}$ domain and a $C_{H3}$ domain, and optionally comprises a $C_{H4}$ domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG).

Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab, Fab', $Fab_2$, $Fab'_2$, IgG, IgM, IgA, IgE, scFv, dsFv, dAb, nanobodies, unibodies, and diabodies. In various embodiments antibodies include, but are not limited to Fab, $Fab_2$, IgG, IgM, IgA, IgE, and single chain Fv (scFv) antibodies in which a variable heavy and a variable light chain are joined together (directly or through a peptide linker) to form a continuous polypeptide.

Diabodies are bivalent antibodies comprising two polypeptide chains, wherein each polypeptide chain comprises $V_H$ and $V_L$ regions joined by a linker that is too short to allow for pairing between two regions on the same chain, thus allowing each region to pair with a complementary region on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

In certain embodiments, antibodies and antibody fragments used in the constructs of the present invention can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al., Proc. Natl. Acad. Sci., USA, 78:5807, 1981), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "chimeric antibody" as used herein refers to an antibody which has framework residues from one species, such as human, and CDRs (which generally confer antigen binding) from another species, such as a murine antibody that specifically binds targeted antigen.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular $CDR_3$. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. All such recombinant means are well known to those of ordinary skill in the art.

An antigen binding protein including an antibody "specifically binds" to an antigen if it binds to the antigen with a high binding affinity as determined by a dissociation constant (Kd, or corresponding Kb, as defined below) value of at least $1 \times 10^{-6}$ M, or at least $1 \times 10^{-7}$ M, or at least $1 \times 10^{-8}$ M, or at least $1 \times 10^{-9}$ M, or at least $1 \times 10^{-10}$ M, or at least $1 \times 10^{-11}$ M. An antigen binding protein that specifically binds to the human antigen of interest may be able to bind to the same antigen of interest from other species as well, with the same or different affinities.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Tumor Associated Antigens and Antibodies

The term "antigen" as used herein refers to a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least three, at least five, or at least eight to ten amino acids in a unique spatial conformation. Methods of determining spatial conformation of epitopes include, for example, x-ray crystallography and 2-dimensional nuclear magnetic resonance.

As relates to "targeted antigens", virtually any antigen may be targeted by the molecules of the present invention. Certain targeted antigens include those associated with a pathology characterized by hyperproliferation of a cell (i.e., a hyperproliferative disorder). Illustrative hyperproliferative disorders include, but are not limited to psoriasis, neutrophilia, polycythemia, thrombocytosis, and cancer. Hyperproliferative disorders characterized as cancer include but are not limited to solid tumors, cancers of the breast, respiratory tract, brain, reproductive organs, digestive tract, urinary tract, eye, liver, skin, head and neck, thyroid, parathyroid and their distant metastases. These disorders also include lymphomas, sarcomas, multiple myelomas and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophtalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

In various embodiments of the present invention, the targeting moiety is a moiety that binds a cancer marker, e.g., a tumor associated antigen (TAA). A wide variety of cancer markers are known to those of skill in the art. The cancer markers need not be unique to cancer cells, but can also be effective where the expression of the cancer marker is elevated in a cancer cell (as compared to normal healthy cells) or where the cancer marker is not present at comparable levels in surrounding tissues (especially where the fusion molecule is delivered locally). In various embodiments the cancer marker includes: Her2/neu (Lewis et al, Semin. Cancer Biol., 6(6): 321-327, 1995), Her3, EGF, Her4, B7 family members (Collins et al., Genome Biol., 6:223.1-223.7, 2005), the TNF superfamily members (see, e.g., "Therapeutic Targets of the TNF Superfamily", edited by Iqbal S. Grewal, Landes Bioscience/Springer Science+Business Media, LLC dual imprint/Springer series: Advances in Experimental Medicine and Biology, 2009), CD1, CD2, CD3, CD5, CD7, CD13, CD14, CD15, CD19, CD20 (Cragg et al., Curr. Dir. Autoimmun., 8: 140-174, 2005), CD21, CD23, CD25, CD33 (Nakase et al., Am J Clin Pathol., 105(6): 761-768, 1996), CD34, CD38, CD46, CD55, CD59, CD123, CD138 (O'Connell, et al., Am. J. Clin. Pathol., 121(2):254-263, 2004), CD200, CD276 (Hofmeyer et al., Proc. Natl. Acad. Sci. (U.S.A.) 105(30):10277-10278, 2008), 5E10, CEA, endoplasmin (U.S. Patent Application No. US20120009194 (Ferrone et al)), HLA-DR, HM 1.24, HMB 45, Ia, Leu-M1, MUC1, PMSA, EGFR, glycosphingolipid GD2, SLAM family members, gp100, tyrosinase, MAGE, TAG-72, SE10, phosphatidyl serine antigen, and the like. The genetically engineered fusion molecules of the present invention may bind one antigen or multiple cancer markers.

Antibodies to these and other cancer markers are known to those of skill in the art and can be obtained commercially or readily produced. For example, antibodies can be produced by immunizing an animal with a target antigen or an immunogenic fragment thereof and raising the antibodies in that animal, and single chain antibodies can be produced using phage-display technology according to methods well known to those of skill in the art. Antibodies contemplated for use as targeting moieties in the fusion molecules of the present invention include depleting antibodies to specific tumor associated antigens, including, but not limited to, anti-HER2/neu, anti-HER3, anti-HER4, anti-CD20, anti-CD19, anti-CD22, anti-CD33, anti-CXCR3, anti-CXCR5, anti-CCR3, anti-CCR4, anti-CCR9, anti-CRTH2, anti-PMCH, anti-CD4, anti-CD25, anti-CD200, anti-CD138, anti-CD276 and anti-endoplasmin antibodies. All such tumor and inflammatory cell-specific, depleting antibodies have been well described in the literature.

In various embodiments the antibody is an anti-Her2/neu antibody which comprises the heavy chain having an amino acid sequence as set forth in SEQ ID NO: 1:

```
                                            (SEQ ID NO: 1)
MECSWVMLFLLSVTAGVHSEVQLVESGGGLVQPGGSLRLSCAASGFNIKD

TYIHWVRQAPGKGLEWVARIYPTNGYTRYADSVKGRFTISADTSKNTAYL

QMNSLRAEDTAVYYCSRWGGDGFYAMDYWGQGTLVTVSSASTKGPSVFPL

APSSKSTSGGTAALGCLVKDYFPEPVTVSWNSGALTSGVHTFPAVLQSSG

LYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPGK
``` wherein amino acid residues 1-19 represent a signal peptide; and the light chain having an amino acid sequence as set forth in SEQ ID NO: 2:

```
                                            (SEQ ID NO: 2)
MEWSCVMLFLLSVTAGVHSDIQMTQSPSSLSASVGDRVTITCRASQDVNT

AVAWYQQKPGKAPKLLIYSASFLYSGVPSRFSGSRSGTDFTLTISSLQPE

DFATYYCQQHYTTPPTFGQGTKVEIKRTVAAPSVFIFEPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC
``` wherein amino acid residues 1-19 represent a signal peptide.

In various embodiments the antibody is an anti-CD20 antibody which comprises the heavy chain having an amino acid sequence as set forth in SEQ ID NO: 3:

```
                                            (SEQ ID NO: 3)
MYLGLNCVIIVFLLKGVQSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSAASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK
``` wherein amino acid residues 1-19 represent a signal peptide; and the light chain having an amino acid sequence as set forth in SEQ ID NO: 4:

(SEQ ID NO: 4)
MKLPVRLLVLMFWIPASSSQIVLSQSPAILSASPGEKVTMTCRASSSVSY

IHWFQQKPGSSPKPWIYATSNLASGVPVRFSGSGSGTSYSLTISRVEAED

AATYYCQQWTSNPPTFGGGTKLEIKRTVAAPSVFIFPPSDEQLKSGTASV

VCLLNNFYPREAKVQWKVDNALQSGNSQESVTEQDSKDSTYSLSSTLTLS

KADYEKHKVYACEVTHQGLSSPVTKSFNRGEC wherein amino acid residues 1-19 represent a signal peptide.

In various embodiments the antibody is an anti-CD138 antibody which comprises the heavy chain having an amino acid sequence as set forth in SEQ ID NO: 5:

(SEQ ID NO: 5)
MGWSYIILFLVATATDVHSQVQLQQSGSELMMPGASVKISCKATGYTFSN

YWIEWVKQRPGHGLEWIGEILPGTGRTIYNEKFKGKATFTADISSNTVQM

QLSSLTSEDSAVYYCARRDYYGNFYYAMDYWGQGTSVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK wherein amino acid residues 1-19 represent a signal peptide; and the light chain having an amino acid sequence as set forth in SEQ ID NO: 6:

(SEQ ID NO: 6)
MDMRVPAQLLGLLLLWLRGARCDIQMTQSTSSLSASLGDRVTISCSASQG

INNYLNWYQQKPDGTVELLIYYTSTLQSGVPSRFSGSGSGTDYSLTISNL

EPEDIGTYYCQQYSKLPRTFGGGTKLEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC wherein amino acid residues 1-22 represent a signal peptide.

In various embodiments the antibody is an anti-endoplasmin antibody which comprises the heavy chain having an amino acid sequence as set forth in SEQ ID NO: 7:

(SEQ ID NO: 7)
MYLGLNCVIIVFLLKGVQSQVQLVQSGAEVKKPGASVKVSCKASGYTFTS

YAMHWVRQAPGQRLEWMGWINAGNGNTKYSQKFQGRVTITRDTSASTAYM

ELSSLRSEDTAVYYCARAHFDYWGQGTLVTVSAASTKGPSVFPLAPSSKS

TSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHN

HYTQKSLSLSPGK wherein amino acid residues 1-19 represent a signal peptide; and the light chain having an amino acid sequence as set forth in SEQ ID NO: 8:

(SEQ ID NO: 8)
MEAPAQLLFLLLLWLPDTTGEIELTQSPSSLSASVGDRVTITCRASQSIS

SYLNWYQQKPGKAPKLLIYAASSLQSGVPSRFSGSGSGTDFTLTISSLQP

EDFATYYCQQSYSTPPTFGQGTKVEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC wherein amino acid residues 1-20 represent a signal peptide.

In various embodiments the antibody is an anti-CD33 antibody which comprises the heavy chain having an amino acid sequence as set forth in SEQ ID NO: 9:

(SEQ ID NO: 9)
MEWSWVFLFFLSVTTGVHSQVQLVQSGAEVKKPGSSVKVSCKASGYTITD

SNIHWVRQAPGQSLEWIGYIYPYNGGTDYNQKFKNRATLTVDNPTNTAYM

ELSSLRSEDTAFYYCVNGNPWLAYWGQGTLVTVSSASTKGPSVFPLAPSS

KSTSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK wherein amino acid residues 1-19 represent a signal peptide; and the light chain having an amino acid sequence as set forth in SEQ ID NO: 10:

(SEQ ID NO: 10)
MSVPTQVLGLLLLWLTDARCDIQLTQSPSTLSASVGDRVTITCRASESLD

NYGIRFLTWFQQKPGKAPKLLMYAASNQGSGVPSRFSGSGSGTEFTLTIS

SLQPDDFATYYCQQTKEVPWSFGQGTKVEVKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC wherein amino acid residues 1-20 represent a signal peptide.

In various embodiments the antibody is an anti-CD276 antibody which comprises the heavy chain variable region having an amino acid sequence as set forth in SEQ ID NO: 11:

(SEQ ID NO: 11)
MNFGFRLIFLALILKGVQCEVQLVESGGGLVKPGGSLKLSCEAS<u>RFTFSS</u>

<u>YA</u>MSWVRQTPEKRLEWVAA<u>ISGGGRYTY</u>YPDSMKGRFTISRDNAKNFLYL

QMSSLRSEDTAMYYC<u>ARHYDGYLDY</u>WGQGTTLTVSSAKTTAPSVYPLAPG

SL wherein amino acid residues 1-19 represent a signal peptide; and the light chain having an amino acid sequence as set forth in SEQ ID NO: 12:

(SEQ ID NO: 12)
MKSQSQVFVFVFLWLSGVDGDIVMTQFAGVDGDIVMTQSHKFMSTSVGDR

VSITCKAS<u>QDVSTT</u>VAWYQQKPGQSPKLLIY<u>SAS</u>YRYTGVPDRFTGSGSG

TDFTFTISSVQAEDLAVYYC<u>QQHYSTPPT</u>FGGGTKLEIKRADAAPTVSIF

PPSSKLG wherein amino acid residues 1-20 represent a signal peptide.

Interferon and Interferon Mutants

The term "interferon" refers to a full-length interferon or to an interferon fragment (truncated interferon) or an interferon mutant (truncated interferon and interferon mutant collectively referred to herein as 'modified interferon'), that substantially retains the biological activity of the full length wild-type interferon (e.g., retains at least 50%). Interferons include type I interferons (e.g., interferon-alpha and interferon-beta) as well as type II interferons (e.g., interferon-gamma). The interferon can be from essentially any mammalian species. U.S. Pat. No. 6,610,830 (Goeddel et al) describes various mature human leukocyte interferons, e.g., interferon-alpha, useful in the treatment or viral and neoplastic diseases.

In various embodiments of the present invention, the interferon mutant comprises one or more amino acid substitutions, insertions, and/or deletions. Means of identifying such modified interferon molecules are routine to those of skill in the art. In one illustrative approach, a library of truncated and/or mutated IFN-α is produced and screened for IFN-α activity. Methods of producing libraries of polypeptide variants are well known to those of skill in the art. Thus, for example error-prone PCR can be used to create a library of mutant and/or truncated IFN-α (see, e.g., U.S. Pat. No. 6,365,408). The resultant library members can then be screened according to standard methods know to those of skill in the art. Thus, for example, IFN-α activity can be assayed by measuring antiviral activity against a particular test virus. Kits for assaying for IFN-α activity are commercially available (see, e.g., ILITE™ alphabeta kit by Neutekbio, Ireland).

The use of chemically modified interferons is also contemplated. For example, in certain embodiments, the interferon is chemically modified to increase serum half-life. Thus, for example, (2-sulfo-9-fluorenylmethoxycarbonyl)-7-interferon-α2 undergoes time-dependent spontaneous hydrolysis, generating active interferon (Shechter et al., Proc. Natl. Acad. Sci., USA, 98(3): 1212-1217, 2001). Other modifications, include for example, N-terminal modifications in including, but not limited to the addition of PEG, protecting groups, and the like (see, e.g., U.S. Pat. No. 5,824,784)

In various embodiments use of truncated interferons is also contemplated. Human INFα, for example, with deletions of the first 15 amino-terminal amino acid residues and/or the last 10-13 carboxyl-terminal amino acid residues, have been shown to exhibit virtually the same activity as the parent molecules (see, e.g., Ackerman (1984) Proc. Natl. Acad. Sci., USA, 81: 1045-1047). Accordingly the use of IFN-αs having 1, 2, 3, up to 13 carboxyl terminal amino acid residues deleted and/or 1, 2, 3, up to 15 amino terminal amino acid residues deleted are contemplated. It has also been demonstrated that activity resides in huIFN-α fragment HuIFN-α (1-110) (Id.). Accordingly carboxyl truncated IFNs with truncations after residue 110 and/or with 1, 2, 3, up to 15 amino terminal amino acid residues deleted are contemplated.

Single point mutations contemplated for use herein include, but are not limited to, a series of mostly single point mutants (see Table 1 below) designed specifically to increase the affinity between IFN-α and IFN-αR and others expected to decrease the affinity between IFN-α and IFN-αR by specifically modeling the changes based on published phage display studies and the NMR structure (Kalie E et al., J. Biol. Chem., 282:11602, 2007; Gomez D and Reich N C, J. Immunol., 170:5373, 2003; Quadt-Akabayov S R et al., Protein Science, 15:2656, 2006; Akabayov S R et al., Biochemistry, 49:687, 2010). The strategy was based on the belief that a single point mutation may change the binding affinity but will not completely knock off the activity of IFN-α, therefore still retaining the antiproliferative properties albeit at much higher concentrations, i.e., the goal is to improve the therapeutic index of fusion molecules comprising the interferon-alpha mutants as compared to fusion molecules comprising wild-type interferon-alpha. As described herein and as depicted in Table 1, a single mutation will be identified by the particular amino acid substitution at a specific amino acid position within the full length wild type interferon sequence. For example, a mutation comprising a tyrosine substituted for the full length wild type histidine at amino acid 57 is identified as H57Y. The wild type IFN-α2 amino acid sequence from which the mutants described in Table 1 are derived is provided below as SEQ ID NO: 13:

(SEQ ID NO: 13)
CDLPQTHSLGSRRTLMLLAQMRRISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEIMRS

FSLSTNLQESLRSKE

TABLE 1

List of certain proposed IFN-α Mutant Molecules.

| | IFN-α sequence mutations | Selection Criteria |
|---|---|---|
| M1 | H57Y, E58N, Q61S | Phage display optimization of selected IFN-α residues to increase IFN-α-IFN-αR1 binding affinity of Site 1 |
| M2 | H57S, E58S, Q61S | Decrease the IFN-α-IFN-αR1 binding affinity at Site 1 based on triple mutations predicted to result in a loss of binding contacts between IFNα and IFN-αR1 |

TABLE 1-continued

List of certain proposed IFN-α Mutant Molecules.

| | IFN-α sequence mutations | Selection Criteria |
|---|---|---|
| M3 | H57A | Decrease the IFN-α-IFN-αR1 binding affinity at Site 1 similar to M2 but only single point |
| M4 | E58A | Decrease the IFN-α-IFN-αR1 binding affinity at Site 1 similar to M2 but only single point |
| M5 | Q61A | Decrease the IFN-α-IFN-αR1 binding affinity at Site 1 similar to M2 but only single point |
| M6 | R149A | Decrease the IFN-α-IFN-αR1 binding affinity at Site 2 based on loss of binding contacts |
| M7 | R162A | Decrease the IFN-α-IFN-αR1 binding affinity at Site 2 based on loss of binding contacts |
| M8 | R149A, R162A | Decrease the IFN-α-IFN-αR1 binding affinity at Site 2 based on loss of binding contacts |
| M9 | L30A | Decrease the IFN-α-IFN-αR1 binding affinity at Site 2 based on loss of binding contacts |
| M10 | D35E | Alter the IFN-α-IFN-αR1 binding at Site 2 based on minimal change in structure |
| M11 | E165D | Alter the IFN-α-IFN-αR1 binding at Site 2 based on minimal change in structure |
| M12 | L26A | Alter the IFN-α-IFN-αR1 binding at Site 2 based on minimal change in structure |
| M13 | F27A | Alter the IFN-α-IFN-αR1 binding at Site 2 based on minimal change in structure |
| M14 | L153A | Alter the IFN-α-IFN-αR1 binding at Site 2 based on minimal change in structure |
| M15 | A145V | Alter the IFN-α-IFN-αR1 binding at Site 2 based on minimal change in structure |

Figure 2:
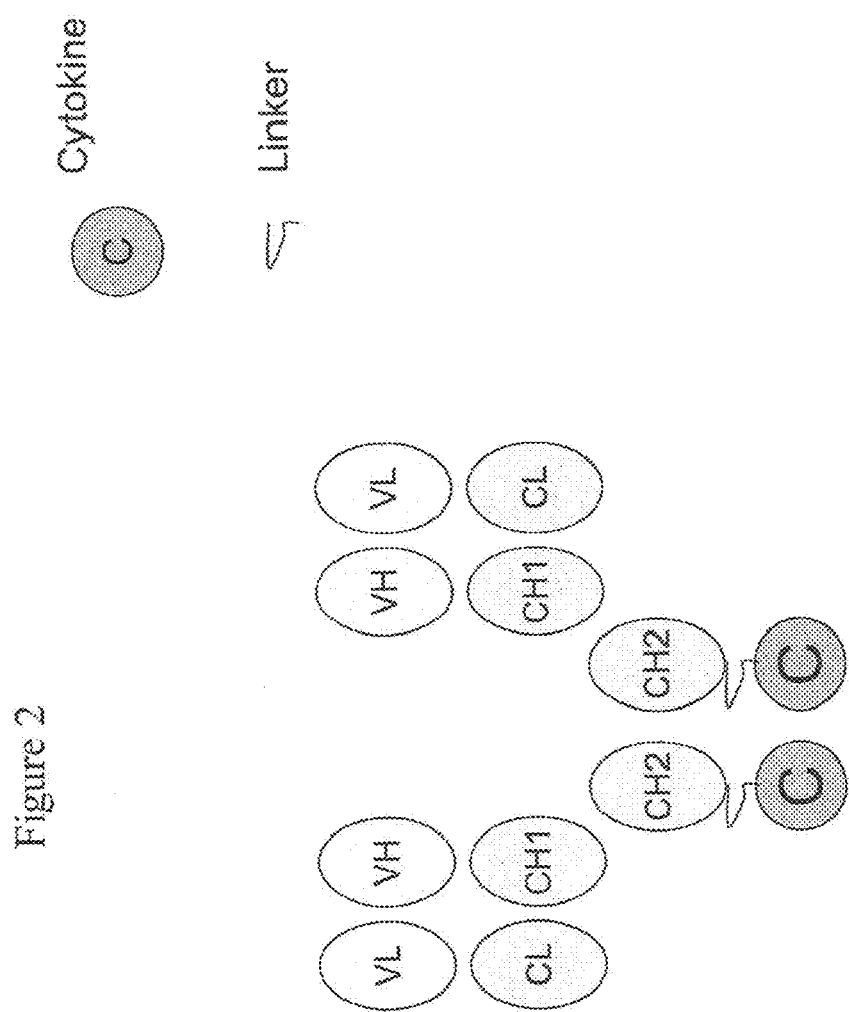
FIG. 2 depicts another proposed design for a genetically engineered fusion molecule of the present invention.
Figure 3:
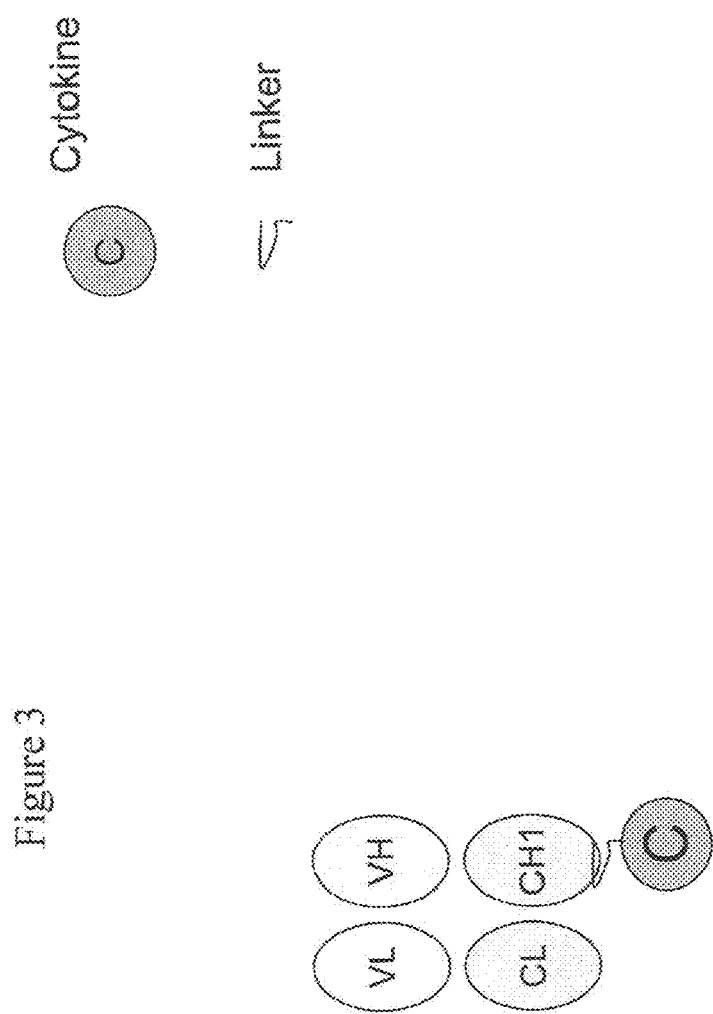
In FIG. 3, the ovals labeled as $V_L$, $V_H$, $C_L$, $C_H$, $C_{H1}$, and $C_{H2}$ represent a Fab$_2$ as defined herein. The oval label C represents a cytokine. A linker is represented by the squiggled line. As depicted in FIG. 3, C is attached to the Fab$_2$ via a linker at the two $C_{H2}$ sites. In one alternative embodiment, C will be attached to the Fab$_2$ via a linker at the two $V_L$ sites rather than the $C_{H2}$ sites. In yet another alternative, C will be attached to the Fab$_2$ via a linker at the two $V_H$ sites rather than two $V_L$ or two $C_{H2}$ sites. In yet another alternative, C will be attached to the Fab$_2$ via a linker at an internal site rather than at the $C_{H2}$, $V_L$, or $V_H$ sites.

In various embodiments of the present invention, either the N- or C-terminus of an antibody heavy or light chain will be genetically constructed with one of several contemplated interferon alpha mutants. The fusion molecule may have any of the general constructs as depicted in, e.g., FIGS. 1-3.

Generally speaking, the antibody and interferon mutant molecule of the genetically engineered fusion molecules of the present invention can be joined together in any order. Thus, for example, the interferon mutant molecule can be joined to either the amino or carboxy terminal of the antibody; or conversely, the interferon mutant molecule can be joined to an internal location of the antibody, so long as the attachment does not interfere with binding of the antibody to the target antigen. Alternatively, the antibody can be joined to either the amino or carboxy terminal of the interferon mutant molecule; or joined to an internal region of the interferon mutant molecule.

The present invention relates to genetically engineered fusion molecules comprising at least one antibody linked to at least one interferon mutant formed through genetic fusion or chemical coupling. By "linked" we mean that the first and second sequences are associated such that the second sequence is able to be transported by the first sequence to a target cell, i.e., fusion molecules in which the antibody is linked to a interferon mutant via their polypeptide backbones through genetic expression of a DNA molecule encoding these proteins, directly synthesized proteins, and coupled proteins in which pre-formed sequences are associated by a cross-linking agent. Many procedures and linker molecules for attachment of various compounds including radionuclide metal chelates, toxins and drugs to proteins such as antibodies are known. See, for example, U.S. Pat. Nos. 4,671,958, 4,659, 839, 4,414,148, 4,699,784; 4,680,338; 4,569,789; and 4,589, 071.

In certain embodiments, the antibody and interferon mutant are linked directly to each other and synthesized using recombinant DNA methodology, e.g., creating a DNA sequence that encodes the antibody-interferon mutant fusion protein, placing the DNA in an expression cassette under the control of a particular promoter, expressing the fusion protein in a host, and isolating the expressed fusion protein. In one embodiment of the present invention, nucleic acid sequences encoding the appropriate antibody framework are optionally cloned and ligated into appropriate vectors (e.g., expression vectors for, e.g., prokaryotic or eukaryotic organisms). Additionally, nucleic acid sequences encoding the appropriate interferon mutant are optionally cloned into the same vector in the appropriate orientation and location so that expression from the vector produces an antibody-interferon mutant fusion molecule. Some optional embodiments also require post-expression modification, e.g., assembly of antibody subunits, etc. The techniques and art for the above (and similar) manipulations are well known to those skilled in the art. Pertinent instructions are found in, e.g., Sambrook et al., Molecular Cloning—A Laboratory Manual (2nd Ed.), Vols. 1-3, Cold Spring Harbor Laboratory, Cold Spring Harbor, N.Y., 1989 and Current Protocols in Molecular Biology, F. M. Ausubel et al., eds., Current Protocols, a joint venture between Greene Publishing Associates, Inc. and John Wiley & Sons, Inc. (supplemented through 1999).

In certain embodiments, the two molecules can be separated by a peptide spacer ("linker") consisting of one or more amino acids. Generally, the peptide linker will have no specific biological activity other than to join the proteins or to preserve some minimum distance or other spatial relationship between them. In certain embodiments, however, the constituent amino acids of the spacer can be selected to influence some property of the molecule such as the folding, net charge, or hydrophobicity. Suitable linkers are well known to those of skill in the art and include, but are not limited to, straight or branched-chain carbon linkers, heterocyclic carbon linkers, or peptide linkers. In certain embodiments, the linker(s) can be joined to the constituent amino acids of the antibody and/or the interferon through their side groups (e.g., through a disulfide linkage to cysteine). In certain embodiments, the linkers are joined to the alpha carbon amino and/or carboxyl groups of the terminal amino acids of the antibody and/or the interferon. In certain embodiments, the linker is a proteolysis-resistant linker such as those described in U.S. Patent Application Publication No. 20100172868 (Morrison et al.). In certain embodiments, the proteolysis-resistant linker is SGGGGS (SEQ ID NO: 14) or AEAAAKEAAAKAGS (SEQ ID NO: 15).

In certain alternative embodiments, the antibody is chemically conjugated to the interferon mutant molecule. Means of chemically conjugating molecules are well known to those of skill. The procedure for conjugating two molecules varies according to the chemical structure of the agent. Polypeptides typically contain variety of functional groups; e.g., carboxylic acid (COOH) or free amine (—NH$_2$) groups, that are available for reaction with a suitable functional group on the other peptide, or on a linker to join the molecules thereto. Alternatively, the antibody and/or the interferon mutant can be derivatized to expose or attach additional reactive functional groups. The derivatization can involve attachment of any of a number of linker molecules such as those available from Pierce Chemical Company, Rockford Ill.

Cells suitable for replicating and for supporting recombinant expression of fusion protein are well known in the art. Such cells may be transfected or transduced as appropriate with the particular expression vector and large quantities of vector containing cells can be grown for seeding large scale fermenters to obtain sufficient quantities of the protein for clinical applications. Such cells may include prokaryotic microorganisms, such as E. coli; various eukaryotic cells, such as Chinese hamster ovary cells (CHO), NSO, 293; HEK Yeast; insect cells; hybridomas; human cell lines; and transgenic animals and transgenic plants, and the like. Standard technologies are known in the art to express foreign genes in these systems. The recombinant protein gene is typically operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

Once expressed, the recombinant fusion proteins can be purified according to standard procedures of the art, including ammonium sulfate precipitation, affinity columns, column chromatography, gel electrophoresis and the like. Substantially pure compositions of at least about 90 to 95% homogeneity are preferred, and 98 to 99% or more homogeneity most preferred for pharmaceutical uses. Once purified, partially or to homogeneity as desired, the polypeptides may then be used therapeutically.

In certain embodiments, the expressed fusion protein may possess a conformation substantially different than the native conformations of the constituent polypeptides and it may thus be necessary to denature and reduce the polypeptide and then cause the polypeptide to re-fold into the conformation. Methods of reducing and denaturing proteins and inducing re-folding are well known to those of skill in the art (see, e.g., Debinski et al., J. Biol. Chem., 268:14065-14070, 1993.

The pharmaceutical compositions of the present invention comprise a genetically engineered fusion molecule of the invention and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Except insofar as any conventional excipient, carrier or vehicle is incompatible with the genetically engineered fusion molecules of the present invention, its' use thereof in the pharmaceutical preparations of the invention is contemplated.

As used herein, the term "administration" refers to the act of giving a drug, prodrug, or other agent, or therapeutic treatment (e.g., radiation therapy) to a physiological system (e.g., a subject or in vivo, in vitro, or ex vivo cells, tissues, and organs). The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. A pharmaceutical composition of the invention is formulated to be compatible with its intended route of administration and therapeutic application. Methods of administering the pharmaceutical compositions of the present invention are via any route capable of delivering the composition to a tumor cell and include, but are not limited to, oral, intradermal, intramuscular, intraperitoneal, intravenous, intratumor, inhalation, subcutaneous, and the like. As will be appreciated by the skilled artisan, the route and/or mode of administration will vary depending upon the desired results. Typical pharmaceutical compositions are in the form of injectable or infusible solutions, such as compositions similar to those used for passive immunization of humans. In one embodiment, the composition is administered by intravenous infusion or injection. In another embodiment, the composition is administered by intramuscular or subcutaneous injection.

The fusion molecules of the present invention and pharmaceutical compositions comprising them can be administered in combination with one or more other therapeutic, diagnostic or prophylactic agents. Additional therapeutic agents include alkylating agents, antimetabolites, immunomodulators, and other anti-neoplastic, anti-tumor, anti-angiogenic or chemotherapeutic agents. Such additional agents may be included in the same composition or administered separately.

Therapeutic pharmaceutical compositions typically must be sterile and stable under the conditions of manufacture and storage. Sterile injectable solutions can be prepared by incorporating the fusion molecule in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the pharmaceutical compositions active compounds may be prepared with a carrier that will protect the composition against rapid release, such as a controlled release composition, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such compositions are patented or generally known to those skilled in the art. See, e.g., Sustained and Controlled Release Drug Delivery Systems, J. R. Robinson, ed., Marcel Dekker, Inc., New York, 1978.

In certain embodiments, the fusion molecules of the present invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet.

For oral therapeutic administration, the fusion molecules can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the pharmaceutical compositions of the present invention. In certain embodiments, the fusion molecule of the invention is co-formulated with and/or co-administered with one or more additional therapeutic agents. These agents include, without limitation, antibodies that bind other targets, antineoplastic agents, antitumor agents, chemotherapeutic agents, and/or other agents known in the art that can enhance an immune response against tumor cells, e.g., IFN-$\beta$1, IL-2, IL-8, IL-12, IL-15, IL-18, IL-23, IFN-$\gamma$, and GM-CSF. Such combination therapies may require lower dosages of the fusion molecule as well as the co-administered agents, thus avoiding possible toxicities or complications associated with the various monotherapies.

The pharmaceutical compositions of the invention may include a "therapeutically effective amount" or a "prophylactically effective amount" of the fusion molecule of the invention. As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the patient's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present invention will be dictated primarily by the unique characteristics of the antibody and the particular therapeutic or prophylactic effect to be achieved.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present invention relates to a method of treating cancer cells in a patient, comprising administering to said patient a therapeutically effective amount (either as monotherapy or in a combination therapy regimen) of a genetically engineered fusion molecule of the present invention in pharmaceutically acceptable carrier, wherein such administration promotes growth inhibition and/or proliferation of a cancer cell. Specifically, the genetically engineered fusion molecules of the present invention are useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, multiple myeloma and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophthalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

This invention also relates to pharmaceutical compositions for inhibiting abnormal cell growth in a mammal comprising an amount of a fusion molecule of the invention in combination with an amount of a chemotherapeutic, wherein the amounts of the fusion molecule and of the chemotherapeutic are together effective in inhibiting abnormal cell growth. Many chemotherapeutics are presently known in the art. Chemotherapeutic agents can be protein or non-protein agents, such as small molecule drugs, antibodies, peptides, proteins, and immunomodulators. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens, and anti-angiogenesis agents. One of skill in the art can readily identify a chemotherapeutic agent (for instance, see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., .COPYRGT. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

The following examples are provided to describe the invention in further detail.

Example 1

This example describes the preparation of genetically engineered fusion molecules comprising a tumor associated antigen antibody and an IFN-α mutant molecule (or wildtype IFN-α molecule).

The fusion molecules of the present invention were prepared using methods and techniques well known and understood by one of ordinary skill in the art and can be generally described as follows: the heavy chain of the antibody was recombinantly engineered with an IFN-α molecule at the carboxy-terminus using a peptide linker, e.g., SGGGGS (SEQ ID NO: 14) or AEAAAKEAAAKAGS (SEQ ID NO: 15). After verifying that the fusion protein vector has the correct nucleotide sequence, it was transfected, along with the antibody light chain vector into CHO cells. Transfectants were screened by ELISA for the production of the complete fusion molecule. The clone giving the highest signal was expanded and following sub-cloning was grown in roller bottles. Conditioned medium was collected, concentrated, and the protein of interest purified using a single Protein A affinity chromatography step or appropriate alternative chromatography methods. The final product was formulated in a desired buffer and at a desired concentration (the protein concentration is confirmed by UV absorption). The purity of the final product was determined by SDS-PAGE both under reducing and non-reducing conditions. Western blot analysis was used to confirm the expected size of the molecule.

In this example, an anti-CD20 antibody comprising the heavy chain having an amino acid sequence as set forth in SEQ ID NO: 3 and the light chain having an amino acid sequence as set forth in SEQ ID NO: 4 was used to prepare Ab-IFN-α fusion molecules comprising wildtype IFN-α (SEQ ID NO: 13) or one of the fifteen IFN-α mutant molecules identified as M1-M15 in Table 1. The molecules were initially constructed as depicted in FIG. 1, with the IFN-α mutant molecules (or wildtype IFN-α) attached via the peptide linker SGGGGS (SEQ ID NO: 14) to the heavy chain of the antibody.

Example 2

This example describes the testing of the anti-CD20Ab-IFN-α mutant fusion molecules of Example 1 at varying doses in various in vitro functional assays to identify anti-CD20Ab-IFN-α mutant fusion molecules with the best therapeutic index. The assays described below are used in the analysis of the anti-CD20Ab-IFN-α mutant fusion molecules.

A. Evaluation of the Ability of the Fusion Molecules to Bind the IFN-αR Complex

Various cell lines and methods previously described in the art will be used to determine the best methodology for assessing the binding of the fusion molecules to the IFN-αR complex. Such methods may include Alexa fluor 555 (Invitrogen), Qdot 565 (Invitrogen), or primary/secondary Ab FACS methodology (Invitrogen). Cells lines to be used may include Daudi cells, U266 cells, and Hel 92.1.7 cells.

Daudi cells are B lymphoblast cells and are very sensitive to the inhibitory effect of IFN-α on cell proliferation. CD20 expression in this cell line is very high, which makes this cell line well suited to track CD20 positive B cell lymphomas. A base medium for Daudi is RPMI with 2 mM L-glutamine, 50 mM b-mercaptoethanol and 10% fetal bovine serum, maintained in an incubator at 37 degrees and 5% carbon dioxide ($CO_2$). Medium has to be replaced every 2-3 days.

U266 is a human myeloma cell line (B lymphocyte cell type) and is very sensitive to the inhibitory effect of IFN-α on cell proliferation. There is no CD20 expression in this cell line, which makes this cell line well suited to be a negative control. A base medium for U266 is RPMI with 2 mM L-glutamine, 50 mM b-mercaptoethanol and 10% fetal bovine serum, maintained in an incubator at 37 degrees and 5% carbon dioxide ($CO_2$). Medium has to be replaced every 2-3 days.

Hel 92.1.7 is a human erythroleukemia cell line, which also has a negative CD20 expression. A base medium for Hel 92.1.7 is RPMI with 2 mM L-glutamine, 50 mM b-mercaptoethanol and 10% fetal bovine serum, maintained in an incubator at 37 degrees and 5% carbon dioxide ($CO_2$). Medium has to be replaced every 2-3 days.

B. Evaluation of the Ability of the Fusion Molecules to Bind Cells Expressing the CD20
Flow Cytometry Analysis To determine the fusion protein binding to the CD20, 38C13-huCD20 cells ($1 \times 10^6$) were incubated with the corresponding anti-CD20Ab-IFN-α mutant fusion proteins or the control reagents. The binding of the fusion proteins was confirmed and compared with the non-fused anti-CD20Ab (RITUXAN® (Genentech)). Cells were reacted with biotinylated rat anti-human IgG (BD Biosciences), followed by PE-labeled streptavidin (BD Biosciences) and then analyzed by flow cytometry using a FACScan (Becton Dickinson) and analyzed using FlowJo software (TreeStar Inc).

C. Evaluation of the Ability of the Fusion Molecules to Bind FCRN Receptor

HuFCRN/B2MG Biotinylation

Purified recombinant HuFCRN/B2MG was solubilized in PBS at a final concentration of 1 mg/ml. NHS-LC-Biotin was prepared in DMSO at a final concentration of 4 mg/ml. For a ≥20-fold molar excess of biotin for a 1 mg/mL protein solution, 4 µl of biotin/DMSO was added to the 1 mg/ml HuFCRN/B2MG protein solution (see http://piercenet.com/instructions/2160237.pdf for complete instructions). Biotinylation was carried out at room temperature for 2 hours and then dialyzed overnight in PBS. The biotinylated reagent was stored at 4° C. at a concentration of 0.1 mg/ml.

HuFCRN/B2MG—Ig:IFN Kinetic Analysis

SA Biosensors were prehydrated in 200 µl of 1× kinetic buffer for 10 minutes in a black 96 well plate. One milliliter of biotinylated HuFCRN/B2MG was prepared at a final concentration of 5 µg/ml in 1× kinetic buffer. Ig:IFN was titrated in 2-fold steps starting at 100 µg/ml for three additional dilutions with final volumes of 200 µl each. The sample plate was set up as follows: during the kinetic determination protocol, the ForteBio Octet instrument measures binding in each well taking readings every 1.6 seconds for 2 minutes. One entire column of four wells (rows A-D) is read in parallel, in real time, before moving to the next column.

Data Processing

The raw data acquired for the interaction between the FCRN/B2MG and the Ig:IFN fusion molecules was processed and fit to a curve in order to extract values of $k_{on}$, $k_{diss}$ and $K_D$. Processing begins with reference correction to compensate for signal drift of the immobilized biosensor with the assay buffer. Y-axis alignment, inter-step correction and savitzky-Golay filtering were applied. Note that various data fitting models may be used depending on the characteristics of the data set. Specific processing settings can vary due to both the experimental setup and analyte-ligand system under investigation. The results of the FCRN/B2MG binding data are as follows:

TABLE 2

|  | Kon | Koff | kD | nM |
|---|---|---|---|---|
| Rituxan | 7.15E+05 | 4.98E−02 | 6.97E−08 | 69.70 |
| wtIFN | 3.55E+05 | 2.01E−02 | 5.67E−08 | 56.70 |
| M1 | 1.38E+05 | 3.11E−03 | 3.96E−08 | 39.60 |
| M2 | 4.10E+04 | 1.64E−03 | 3.99E−08 | 39.90 |
| M3 | 5.23E+04 | 9.63E−04 | 1.84E−08 | 18.40 |
| M4 | 7.10E+04 | 7.90E−04 | 1.11E−08 | 11.10 |
| M5 | 3.21E+05 | 1.51E−02 | 4.71E−08 | 47.10 |
| M6 | 2.46E+04 | 4.92E−04 | 2.00E−08 | 20.00 |
| M7 | 8.72E+03 | 3.24E−04 | 3.72E−08 | 37.20 |
| M8 | 1.19E+04 | 1.69E−04 | 1.42E−08 | 14.20 |
| M9 | 2.59E+04 | 5.92E−04 | 2.29E−08 | 22.90 |
| M10 | 3.89E+05 | 2.08E−02 | 5.35E−08 | 53.50 |
| M11 | 4.05E+05 | 1.93E−02 | 4.76E−08 | 47.60 |
| M12 | 3.04E+05 | 2.78E−02 | 9.14E−08 | 91.40 |
| M13 | 8.09E+03 | 2.20E−04 | 2.72E−08 | 27.20 |
| M14 | 3.78E+05 | 2.08E−02 | 5.51E−08 | 55.10 |
| M15 | 3.73E+05 | 1.74E−02 | 4.66E−08 | 46.60 |

The neonatal FcR (FcRn) binds to the Fc domain of IgG at acidic pH in the endosome and protects IgG from degradation, thereby contributing to the long serum half-life of IgG. To understand the pharmacokinetics behavior of mutant fusion proteins, we determined the binding of to all fifteen mutant fusion proteins to recombinant FcRn in vitro. Binding affinities in terms of $K_{on}$, $K_{off}$ and KD values for each mutant fusion protein to FcRn/B2MG were calculated and presented in the above table. A profound effect of IFN-α mutations on the affinities of these mutant fusion proteins to FcRn was clearly evident, which manifested as either improvement or decrease in the binding affinity as compared to the wild-type IFN-α fusion protein, suggesting the important role played by various mutations to affect the ability of the binding of the fusion proteins to FcRn. This profound effect on FcRn binding by simple mutations in the IFN-α payload attached at the C-terminal of the heavy chains of the antibodies, at a site distal from the FcRn binding to the Fc domain, is completely unexpected and a surprising finding. As binding affinity of FcRn to the Fc portion of the antibodies has been shown to correlate with the serum half-lives (Yeung et al., J. Immunol., 182:7663-7671, 2009), this effect of mutations in the IFN-α payload may regulate serum half-lives of fusion protein. Thus, this novel finding of strong influence of IFN-α mutations in altering the FcRn binding affinity teaches us a completely new way to optimize the PK properties of our fusion proteins, and molecules with improved PK properties are provided herein.

D. Evaluation of the IFN Bioactivity of the Fusion Molecules

To assess the anti-viral activity of the anti-CD20Ab-IFN-α mutant fusion proteins, WISH cells (transformed human cell line of epitheloid morphology) were seeded at $2 \times 10^5$ cells/ml and treated with two-fold serial dilutions of the fusion proteins or Roferon® (recombinant human interferon alpha-2a) for 24 hrs. Cells were then infected with VSV (vesicular stomatitis virus) at a concentration of 4000 pfu/100 µl. After 72 hrs, cells were stained with 0.1% crystal violet. Protection against viral infection was determined either by quantitating the cells surviving the infection by staining with 0.1% crystal violet and determining the amount of dye in each well using a spot densitometer of by counting the number of plaques.

E. Evaluation of the Antiproliferative Activity of the Fusion Molecules

Assays such as those described below are to be used in the antiproliferative activity analysis of the anti-CD20Ab-IFN-α mutant fusion molecules.

MTS Assay for the Antiproliferative Activity of Fusion Proteins

Tumor cells were plated in a 96-well tissue culture plate at a density of $1.25 \times 10^4$ cells/well and serial dilutions of different fusion proteins added. After 48 hrs at 37° C. in a 5% $CO_2$ atmosphere, plates were developed by addition of 20 µl of MTS solution (Promega, Madison, Wis.) and measured on an ELISA reader at 490 nm. Percent inhibition of proliferation was calculated.

$^3$H-Thymidine Incorporation to Measure Antiproliferative Effects

Tumor cells were plated in a 96-well tissue culture plate at a density of $1.25 \times 10^4$ cells/well and serial dilutions of different fusion proteins added. After 24 hr, [methyl-$^3$H]-thymidine (ICN Biomedicals, Inc., Irvine, Calif.) was added to a final concentration of 4 µCi/ml. Cells were cultured for an additional 24 hr and then harvested onto glass fiber filters using a 11050 Micro Cell Harvester, (Skatron, Norway) and counted in a 1205 Betaplate Liquid Scintillation Counter (WALLAC Inc., Gaithersburg, Md.) and the percent inhibition of proliferation calculated.

Inhibition of Proliferation of CFSE Labeled Tumor Cells

Tumor cells ($1 \times 10^6$) were incubated with 2.5 µM CFSE (Molecular Probes) for 10 min at 37° C. Cells were then treated with 1 nM of different fusion proteins for 48 hours, and analyzed by flow cytometry following procedures suggested by the manufacturer, using the CellTrace™ CFSE Cell Proliferation Kit (Molecular Probes).

F. Evaluation of the Ability of the Fusion Molecules to Induce Apoptosis

Assays such as the assays described below is to be used in the analysis of the anti-CD20Ab-IFN-α mutant fusion molecule's ability to induce apoptosis.

Determination of Apoptosis

Tumor cells (1×10⁶) were treated with different fusion proteins for 72 hours. The cells were then washed with ice-cold PBS. The Annexin V/propidium iodide (PI) assay was conducted using the Vybrant Apoptosis Assay Kit #2 following procedures suggested by the manufacturer (Molecular Probe). The percentage of apoptotic cells was calculated as the sum of the percentages of early apoptotic cells and late apoptotic cells.

Example 3

This example describes in vivo studies using Ab-IFN-α mutant fusion molecules which demonstrated increased binding affinity for the FcRn receptor in the in vitro assays to determine whether such Ab-IFN-α mutant fusion molecules demonstrate improved PK properties. The assay described below is used in the analysis of the Ab-IFN-α mutant fusion molecules.

Murine rIFN-α (PBL Biomedical Laboratories), IgG3-IFN-α, and anti-CD20Ab-IFN-α mutant fusion proteins were iodinated to 10 µCi/µg with $^{125}$I using Iodo-Beads (Pierce) according to the manufacturer's protocol. Mice were injected i.p. with 66 µCi of $^{125}$I-labeled proteins. At various intervals after injection of $^{125}$I-labeled rIFN-α, IgG3-IFN-α, or anti-CD20Ab-IFN-α mutant fusion protein residual radioactivity was measured using a mouse whole body counter (Wm. B. Johnson and Associates).

Example 4

This example describes in vivo studies using Ab-IFN-α mutant fusion molecules which demonstrated improved therapeutic index in the in vitro assays (Example 2) to determine efficacy in treating in vivo tumors. Assays such as those described below are to be used in the analysis of the anti-CD20Ab-IFN-α mutant fusion molecules.

Mice (groups of 4) were injected subcutaneously with 5000 38C13-CD20 cells on day zero. On days 1, 2 and 3 they were treated intravenously with hepes buffered saline solution (HBSS) or 0.4 µg, 2 µg, or 10 µg of anti-CD20Ab-IFN-α mutant fusion molecules and tumor growth monitored.

C3H/HeJ mice were inoculated with 5000 38C13-CD20 cells on day 0. On days 5, 6 and 7 they were treated with HBSS or 10 µg of anti-CD20Ab-IFN-α mutant fusion molecules. They were monitored for tumor growth and survival.

C3H/H3J mice were inoculated with 5000 38C13-CD20 cells on day 0 and treated on days 5, 6 and 7 with 10 µg of anti-CD20-IgG3, or 10 µg of anti-CD20Ab-IFN-α mutant fusion molecules and followed for tumor growth and survival.

Example 5

In this example, a fusion molecule comprising: 1) an anti-CD33 antibody and wildtype IFN-α molecule; 2) an anti-CD33 antibody and the IFN-α mutant molecule M1 of Table 1; 3) an anti-CD33 antibody and the IFN-α mutant molecule M8 of Table 1; and 4) an anti-CD33 antibody and the IFN-α mutant molecule M13 of Table 1 were constructed as depicted in FIG. 1 and as described in Example 1. In the fusion molecule constructs of this embodiment, the wildtype IFN-α molecule comprised the amino acid sequence depicted in SEQ ID NO: 13. Constructs were made using the peptide linker SGGGGS (SEQ ID NO: 14), and constructs were made using the peptide linker AEAAAKEAAAKAGS (SEQ ID NO: 15). The anti-CD33 antibody comprised the heavy chain amino acid sequence and light chain amino acid sequence depicted in SEQ ID NO: 9 and SEQ ID NO: 10, respectfully.

The various fusion molecules were tested in various in vitro functional assays to identify anti-CD33Ab-IFN-α mutant fusion molecules with the best therapeutic index and preserved or improved efficacy in vivo as compared to that of an anti-CD33Ab-wtIFN-α fusion molecule, and the fusion molecule which demonstrated the best PK properties.

Example 6

In this example, a fusion molecule comprising: 1) an anti-CD138 antibody and wildtype IFN-α molecule; 2) an anti-CD138 antibody and the IFN-α mutant molecule M1 of Table 1; 3) an anti-CD138 antibody and the IFN-α mutant molecule M8 of Table 1; and 4) an anti-CD138 antibody and the IFN-α mutant molecule M13 of Table 1 were constructed as depicted in FIG. 1 and as described in Example 1. In the fusion molecule constructs of this embodiment, the wildtype IFN-α molecule comprised the amino acid sequence depicted in SEQ ID NO: 13. Constructs were made using the peptide linker SGGGGS (SEQ ID NO: 14), and constructs were made using the peptide linker AEAAAKEAAAKAGS (SEQ ID NO: 15). The anti-CD138 antibody comprised the heavy chain amino acid sequence and light chain amino acid sequence depicted in SEQ ID NO: 5 and SEQ ID NO: 6, respectfully.

The various fusion molecules were tested in various in vitro functional assays to identify anti-CD138 Ab-IFN-α mutant fusion molecules with the best therapeutic index and preserved or improved efficacy in vivo as compared to that of an anti-CD138Ab-wtIFN-α fusion molecule, and the fusion molecule which demonstrated the best PK properties.

Example 7

In this example, a fusion molecule comprising: 1) an anti-HER2/neu antibody and wildtype IFN-α molecule; 2) an anti-HER2/neu antibody and the IFN-α mutant molecule M1 of Table 1; 3) an anti-HER2/neu antibody and the IFN-α mutant molecule M8 of Table 1; and 4) an anti-HER2/neu antibody and the IFN-α mutant molecule M13 of Table 1 were constructed as depicted in FIG. 1 and as described in Example 1. In the fusion molecule constructs of this embodiment, the wildtype IFN-α molecule comprised the amino acid sequence depicted in SEQ ID NO: 13. Constructs were made using the peptide linker SGGGGS (SEQ ID NO: 14), and constructs were made using the peptide linker AEAAAKEAAAKAGS (SEQ ID NO: 15). The anti-HER2/neu antibody comprised the heavy chain amino acid sequence and light chain amino acid sequence depicted in SEQ ID NO: 1 and SEQ ID NO: 2, respectfully.

The various fusion molecules were tested in various in vitro functional assays to identify anti-HER2/neu Ab-IFN-α mutant fusion molecules with the best therapeutic index and preserved or improved efficacy in vivo as compared to that of an anti-HER2/neu Ab-wtIFN-α fusion molecule, and the fusion molecule which demonstrated the best PK properties.

Example 8

In this example, a fusion molecule comprising: 1) an anti-endoplasmin antibody and wildtype IFN-α molecule; 2) an anti-endoplasmin antibody and the IFN-α mutant molecule M1 of Table 1; 3) an anti-endoplasmin antibody and the IFN-α mutant molecule M8 of Table 1; and 4) an anti-endoplasmin antibody and the IFN-α mutant molecule M13 of Table 1 were constructed as depicted in FIG. 1 and as described in Example 1. In the fusion molecule constructs of this embodiment, the wildtype IFN-α molecule comprised the amino acid sequence depicted in SEQ ID NO: 13. Constructs were made using the peptide linker SGGGGS (SEQ ID NO: 14), and constructs were made using the peptide linker AEAAAKEAAAKAGS (SEQ ID NO: 15). The anti-endoplasmin antibody comprised the heavy chain amino acid sequence and light chain amino acid sequence depicted in SEQ ID NO: 7 and SEQ ID NO: 8, respectfully.

The various fusion molecules were tested in various in vitro functional assays to identify anti-endoplasmin Ab-IFN-α mutant fusion molecules with the best therapeutic index and preserved or improved efficacy in vivo as compared to that of an anti-endoplasmin Ab-wtIFN-α fusion molecule, and the fusion molecule which demonstrated the best PK properties.

Example 9

In this example, a fusion molecule comprising: 1) an anti-CD276 antibody and wildtype IFN-α molecule; 2) an anti-CD276 antibody and the IFN-α mutant molecule M1 of Table 1; 3) an anti-CD276 antibody and the IFN-α mutant molecule M8 of Table 1; and 4) an anti-CD276 antibody and the IFN-α mutant molecule M13 of Table 1 were constructed as depicted in FIG. 1 and as described in Example 1. In the fusion molecule constructs of this embodiment, the wildtype IFN-α molecule comprised the amino acid sequence depicted in SEQ ID NO: 13. Constructs were made using the peptide linker SGGGGS (SEQ ID NO: 14), and constructs were made using the peptide linker AEAAAKEAAAKAGS (SEQ ID NO: 15). The anti-CD276 antibody comprised the heavy chain variable region amino acid sequence and light chain variable region amino acid sequence depicted in SEQ ID NO: 11 and SEQ ID NO: 12, respectfully.

The various fusion molecules were tested in various in vitro functional assays to identify anti-CD276 Ab-IFN-α mutant fusion molecules with the best therapeutic index and preserved or improved efficacy in vivo as compared to that of an anti-CD276 Ab-wtIFN-α fusion molecule, and the fusion molecule which demonstrated the best PK properties.

All of the articles and methods disclosed and claimed herein can be made and executed without undue experimentation in light of the present disclosure. While the articles and methods of this invention have been described in terms of various embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by certain embodiments and optional features, modification and variation of the concepts herein disclosed may be resorted to by those skilled in the art, and that such modifications and variations are considered to be within the scope of this invention as defined by the appended claims.

What is claimed is:

1. A genetically engineered fusion molecule comprising a tumor-associated antigen (TAA) antibody (Ab) attached to an interferon alpha (IFN-α) mutant molecule, wherein said antibody is attached directly to said IFN-α mutant molecule, wherein said IFN-α mutant molecule is a mutated human IFN-α2 molecule comprising at least one mutation in SEQ ID NO: 13, wherein said mutation is selected from H57A, E58A, L30A, and F27A, and wherein the TAA antibody is an IgG antibody.

2. A fusion molecule of claim 1, wherein said fusion molecule demonstrates improved pharmacokinetics (PK) properties as compared to a TAA Ab-wildtype_IFN-α fusion molecule.

3. A fusion molecule of claim 1, wherein said fusion molecule when contacted to a tumor cell results in the killing or inhibition of growth or proliferation of said tumor cell.

4. A fusion molecule of claim 1, wherein said TAA antibody is an antibody selected from the group consisting of anti-HER2/neu, anti-HER3, anti-HER4, anti-CD4, anti-CD19, anti-CD20, anti-CD22, anti-CD25, anti-CD33, anti-CD138, anti-CD200, anti-CD276, anti-CXCR3, anti-CXCR5, anti-CCR3, anti-CCR4, anti-CCR9, anti-CRTH2, anti-PMCH, and anti-endoplasmin antibody.

5. A fusion molecule of claim 1, wherein the TAA antibody is an anti-HER2/neu antibody and wherein the mutated human IFN-α2 molecule comprises the mutation F27A in SEQ ID NO: 13.

6. A fusion molecule of claim 1, wherein the TAA antibody is an anti-CD20 antibody and wherein the mutated human IFN-α2 molecule comprises the mutation F27A in SEQ ID NO: 13.

7. A fusion molecule of claim 1, wherein the TAA antibody is an anti-CD138 antibody and wherein the mutated human IFN-α2 molecule comprises the mutation F27A in SEQ ID NO: 13.

8. A fusion molecule of claim 1, wherein the TAA antibody is an anti-endoplasmin antibody and wherein the mutated human IFN-α2 molecule comprises the mutation F27A in SEQ ID NO: 13.

9. A fusion molecule of claim 1, wherein the TAA antibody is an anti-CD33 antibody and wherein the mutated human IFN-α2 molecule comprises the mutation F27A in SEQ ID NO: 13.

10. A fusion molecule of claim 1, wherein the TAA antibody is an anti-CD276 antibody and wherein the mutated human IFN-α2 molecule comprises the mutation F27A in SEQ ID NO: 13.

11. A fusion molecule of claim 1, wherein the TAA antibody is an anti-HER2/neu antibody and wherein the mutated human IFN-α2 molecule comprises the two mutations R149A and R162A in SEQ ID NO: 13.

12. A fusion molecule of claim 1, wherein the TAA antibody is an anti-CD20 antibody and wherein the mutated human IFN-α2 molecule comprises the two mutations R149A and R162A in SEQ ID NO: 13.

13. A fusion molecule of claim 1, wherein the TAA antibody is an anti-CD138 antibody and wherein the mutated human IFN-α2 molecule comprises the two mutations R149A and R162A in SEQ ID NO: 13.

14. A fusion molecule of claim 1, wherein the TAA antibody is an anti-endoplasmin antibody and wherein the mutated human IFN-α2 molecule comprises the two mutations R149A and R162A in SEQ ID NO: 13.

15. A fusion molecule of claim 1, wherein the TAA antibody is an anti-CD33 antibody and wherein the mutated human IFN-α2 molecule comprises the two mutations R149A and R162A in SEQ ID NO: 13.

16. A fusion molecule of claim 1, wherein the TAA antibody is an anti-CD276 antibody and wherein the mutated human IFN-α2 molecule comprises the two mutations R149A and R162A in SEQ ID NO: 13.

17. A fusion molecule of claim 1, wherein the TAA antibody is an anti-HER2/neu antibody and wherein the mutated human IFN-α2 molecule comprises the mutation R162A in SEQ ID NO: 13.

18. A fusion molecule of claim 1, wherein the TAA antibody is an anti-CD20 antibody and wherein the mutated human IFN-α2 molecule comprises the mutation R162A in SEQ ID NO: 13.

19. A fusion molecule of claim 1, wherein the TAA antibody is an anti-CD138 antibody and wherein the mutated human IFN-α2 molecule comprises the mutation R162A in SEQ ID NO: 13.

20. A fusion molecule of claim 1, wherein the TAA antibody is an anti-endoplasmin antibody and wherein the mutated human IFN-α2 molecule comprises the mutation R162A in SEQ ID NO: 13.

21. A fusion molecule of claim 1, wherein the TAA antibody is an anti-CD33 antibody and wherein the mutated human IFN-α2 molecule comprises the mutation R162A in SEQ ID NO: 13.

22. A fusion molecule of claim 1, wherein the TAA antibody is an anti-CD276 antibody and wherein the mutated human IFN-α2 molecule comprises the mutation R162A in SEQ ID NO: 13.

23. A fusion molecule of claim 1, wherein said antibody is directly joined attached to said interferon mutant molecule with a peptide linker, wherein said peptide linker is selected from SEQ ID NO: 14 and SEQ ID NO: 15.

24. A pharmaceutical composition comprising a fusion molecule of claim 1 in a pharmaceutically acceptable carrier.

* * * * *